(12) United States Patent
Yue

(10) Patent No.: US 8,172,878 B2
(45) Date of Patent: May 8, 2012

(54) CONICAL INTERSPINOUS APPARATUS AND A METHOD OF PERFORMING INTERSPINOUS DISTRACTION

(76) Inventor: James J. Yue, Guilford, CT (US)

( * ) Notice: Subject to any disclaimer, the term of this patent is extended or adjusted under 35 U.S.C. 154(b) by 572 days.

(21) Appl. No.: 12/343,082

(22) Filed: Dec. 23, 2008

(65) Prior Publication Data

US 2010/0057130 A1 Mar. 4, 2010

Related U.S. Application Data

(60) Provisional application No. 61/092,142, filed on Aug. 27, 2008.

(51) Int. Cl.
*A61B 17/70* (2006.01)
(52) U.S. Cl. .......................... 606/249; 606/248; 606/90
(58) Field of Classification Search ................ 606/248, 606/249, 279, 90, 104, 99; 623/17.11–17.16
See application file for complete search history.

(56) References Cited

U.S. PATENT DOCUMENTS

| | | | |
|---|---|---|---|
| 5,609,634 A | 3/1997 | Voydeville | |
| 5,645,599 A | 7/1997 | Samani | |
| 5,836,948 A | 11/1998 | Zucherman et al. | |
| 5,860,977 A | 1/1999 | Zucherman et al. | |
| 5,876,404 A | 3/1999 | Zucherman et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,090,112 A | 7/2000 | Zucherman et al. | |
| 6,152,926 A | 11/2000 | Zucherman et al. | |
| 6,156,038 A | 12/2000 | Zucherman et al. | |
| 6,183,471 B1 | 2/2001 | Zucherman et al. | |
| 6,190,387 B1 | 2/2001 | Zucherman et al. | |
| 6,235,030 B1 | 5/2001 | Zucherman et al. | |
| 6,238,397 B1 | 5/2001 | Zucherman et al. | |
| 6,332,883 B1 | 12/2001 | Zucherman et al. | |
| 6,419,677 B2 | 7/2002 | Zucherman et al. | |
| 6,440,169 B1 | 8/2002 | Elberg et al. | |
| 6,451,020 B1 | 9/2002 | Zucherman et al. | |
| 6,478,796 B2 | 11/2002 | Zucherman et al. | |
| 6,514,256 B2 | 2/2003 | Zucherman et al. | |
| 6,733,534 B2 | 5/2004 | Sherman | |
| 2001/0012938 A1 | 8/2001 | Zucherman et al. | |
| 2001/0016743 A1 | 8/2001 | Zucherman et al. | |

(Continued)

FOREIGN PATENT DOCUMENTS

EP 1920719 5/2008

(Continued)

*Primary Examiner* — Eduardo C Robert
*Assistant Examiner* — Christina Negrelli
(74) *Attorney, Agent, or Firm* — Michael R. Shevlin

(57) ABSTRACT

A conical interspinous apparatus includes a distractor comprising an insertion portion and a central engagement groove, the insertion portion having a conical shape which tapers to a tip and is adapted to enable passage of the distractor between two spinous processes of vertebrae, and the central engagement groove is adapted to secure the distractor between the two spinous processes such that the two spinous processes rest in the central engagement groove. The conical interspinous apparatus includes a stabilizer which is adapted to be deployed from within the distractor to secure the two spinous processes within the central engagement groove and an insertion driver detachably coupled to a rear portion of the distractor. A guide wire, having a pointed tip, aids in the insertion of the distractor between the two spinous processes and is configured to guide the insertion of the distractor.

29 Claims, 19 Drawing Sheets

U.S. PATENT DOCUMENTS

| | | |
|---|---|---|
| 2001/0016776 A1 | 8/2001 | Zucherman et al. |
| 2003/0114854 A1 | 6/2003 | Pavlov et al. |
| 2005/0165398 A1 | 7/2005 | Reiley |
| 2006/0264938 A1 | 11/2006 | Zucherman et al. |
| 2006/0265066 A1 | 11/2006 | Zuckerman |
| 2006/0271049 A1 | 11/2006 | Zucherman et al. |
| 2007/0055237 A1 | 3/2007 | Edidin et al. |
| 2007/0149972 A1 | 6/2007 | Nakajima et al. |
| 2008/0027438 A1 | 1/2008 | Abdou |
| 2008/0045958 A1 | 2/2008 | Zucherman et al. |
| 2008/0058935 A1 | 3/2008 | Malandain |
| 2008/0071280 A1 | 3/2008 | Winslow |
| 2008/0161822 A1 | 7/2008 | Perez-Cruet et al. |
| 2008/0177312 A1 | 7/2008 | Perez-Cruet et al. |
| 2008/0243250 A1* | 10/2008 | Seifert et al. ............... 623/17.16 |
| 2009/0326581 A1* | 12/2009 | Galley et al. .................. 606/249 |

FOREIGN PATENT DOCUMENTS

| | | |
|---|---|---|
| GB | 2436293 | 9/2007 |
| WO | WO 2006/064356 | 6/2006 |

* cited by examiner

CONICAL INTERSPINOUS APPARATUS AND A METHOD OF PERFORMING INTERSPINOUS DISTRACTION

CROSS-REFERENCE TO RELATED APPLICATION

The present application claims priority from U.S. Provisional Application No. 61/092,142, which was filed on Aug. 27, 2008, and is incorporated herein by reference in its entirety.

BACKGROUND OF THE INVENTION

1. Field of the Invention

The present invention relates to the field of interspinous devices, and more particularly, relates to conical interspinous apparatus inserted between two spinous processes of the lumbar spine such that the two spinous processes are separated, the spinal canal opens and the symptoms of spinal stenosis are alleviated. Thus, the conical interspinous apparatus can be used to treat spinal stenosis.

2. Description of the Related Art

Lumbar Spinal Stenosis (LSS) is one of the most common reasons for spine surgery in older people. Spinal stenosis is a medical condition in which the spinal canal narrows and compresses the spinal cord and nerves. This is usually due to the natural process of spinal degeneration that occurs with aging. It can also sometimes be caused by spinal disc herniation, osteoporosis or a tumor. Spinal stenosis may affect the cervical or lumbar vertebrae or both. Lumbar spinal stenosis results in lower back pain as well as pain or abnormal sensations in the legs, thighs, feet or buttocks, or loss of bladder and bowel control.

Laminectomy is a basic part of the surgical treatment of LSS and is the most effective remedy for severe spinal stenosis. Laminectomy can be done without spinal fusion. However, if the spinal column is unstable, fusion may be required for the laminectomy.

Therefore, a device which can be implanted between two spinous processes of the spine more easily and which involves less invasive procedures than present day procedures is needed. Also, a device which can easily be adapted for both fusion and non-fusion procedures is needed. Such a device would aid in the treatment for spinal stenosis.

SUMMARY OF THE INVENTION

Exemplary embodiments of the present invention overcome the above disadvantages and other disadvantages not described above. Also, the present invention is not required to overcome the disadvantages described above, and an exemplary embodiment of the present invention may not overcome any of the problems described above. The present invention provides conical interspinous apparatus inserted between two spinous processes of the lumbar spine such that the two spinous processes are separated, and a method of performing interspinous distraction.

According to an exemplary embodiment of the present invention, there is provided a conical interspinous apparatus including a distractor having an insertion portion and a central engagement groove having a proximal end and a distal end, the insertion portion having a conical shape which tapers from the proximal end of the central engagement groove to a tip and is adapted to enable passage of the distractor between two spinous processes of vertebrae such that a gradual distraction between the two spinous processes occurs, and the central engagement groove is adapted to secure the distractor between the two spinous processes such that the two spinous processes rest in the central engagement groove between the proximal end and the distal end; a stabilizer which is adapted to be deployed from the distractor to secure the two spinous processes within the central engagement groove; an insertion driver detachably coupled to a rear portion of the distractor; and a guide wire having a pointed tip, the guide wire being adapted for insertion between the two spinous processes and configured to guide the insertion of the distractor, coupled to the insertion driver, between the two spinous processes, wherein the distractor and the insertion driver each have a guide channel extending through an entire central portion therein, each guide channel being in alignment with each other and configured to accept the guide wire therein.

The insertion portion has an axis of distraction having a constant increasing angle that provides for constant distraction. Furthermore, the insertion portion may have a conical screw shape such that a surface of the insertion portion has screw-shaped (i.e., helical) grooves adapted to enable the distractor to be screwed into place between the two spinous processes. If the insertion portion is created with a grooved surface, the grooves can be created with a differential pitch and thread design.

The tip of the insertion portion may also be grooved. On the other hand, the tip of the insertion portion may be ungrooved to allow for ease of initial insertion and the remaining portions of the insertion portion are grooved to permit gradual distraction and stabilization of device after insertion.

The distractor can be composed of any solid or semi solid material including but not limited to poly-ether-ether-ketone (PEEK), titanium, stainless steel, or bone. In addition, the distractor may be composed of but not limited to hydroxyapatite, bone substitutes, a combination of hydroxyapatite and bone cement, CORTOSS, or the like. If the distractor is composed of any material besides bone, motion is preserved due to the rolling effect of the cone in extension and flexion. If the distractor is composed of bone, the device can be used to induce fusion. Thus, the device could also be used to fuse spines depending on what material it is made of.

Furthermore, a non-bone insertion portion may be composed of differing materials to permit for a collapsing umbrella stabilizing tip to be deployed, to be described below.

The stabilizer includes a wire fed through the guide channel and connected to the tip of the insertion portion; and the insertion portion, made of flexible material and having a first diameter at the proximal end of the central engagement groove. The insertions portion is configured to flex outward and collapse towards the proximal end of the central engagement groove such that the insertion portion is compressed into a shape having a second diameter at the proximal end of the central engagement groove larger than the first diameter to inhibit the distractor from reversing out from between the two spinous processes, the tip of the insertion portion is adapted to be pulled towards the central engagement groove upon pulling of the wire to collapse the insertion portion.

The stabilizer may further include a stabilization base coupled to the distal end of the central engagement groove and which extends outward from the distractor and is adapted to inhibit the distractor from being inserted further between the two spinous processes.

According to another exemplary embodiment of the present invention, there is provided a stabilizer including a pair of proximal stabilization wings retracted within a first cavity of the distractor and configured to be deployed through a pair of proximal slots disposed on opposite sides of the proximal end of the central engagement groove; and an insertion screw driver inserted within the guide channel of the distractor, coupled to the insertion driver and configured to engage a first pair of gears, each gear of the first pair of gears mechanically coupled to one of the pair of proximal stabilization wings, wherein when the insertion driver is turned, the insertion screw driver is turned within the distractor and engages with the first pair of gears to deploy the pair of proximal stabilization wings from the proximal slots.

The stabilizer may further include a pair of distal stabilization wings retracted within a second cavity of the distractor and configured to be deployed through a pair of distal slots disposed on opposite sides of the distal end of the central engagement groove; and the insertion screw driver is configured to engage a second pair of gears, each gear of the second pair of gears mechanically coupled to one of the pair of distal stabilization wings, wherein when the insertion driver is turned, the insertion screw driver is turned within the distractor and engages with the second pair of gears to deploy the pair of distal stabilization wings from the distal slots.

The stabilizer may further include a stabilization base coupled to the distal end of the central engagement groove and which extends outward from the distractor and is adapted to inhibit the distractor from being inserted further between the two spinous processes.

According to another exemplary embodiment of the present invention, there is provided a stabilizer including a pair of proximal stabilization wings retracted within a first cavity of the distractor and configured to be deployed through a pair of proximal slots disposed on opposite sides of the proximal end of the central engagement groove; a pair of distal stabilization wings retracted within a second cavity of the distractor and configured to be deployed through a pair of distal slots disposed on opposite sides of the distal end of the central engagement groove; and a deployment bar coupled to the insertion driver and to each stabilization wing of the proximal stabilization wings and the distal stabilization wings, the deployment bar being inserted within the guide channel of the distractor, and configured to be slidably switched between an extended position and a retracted position, wherein, when in the extended position, the deployment bar maintains the proximal stabilization wings and the distal stabilization wings in a retracted state, and, when in the retracted position, the deployment bar releases the proximal stabilization wings and the distal stabilization wings from the distractor to a deployed state.

The stabilizer may further include a lock configured to engage with the deployment bar while in the retracted position and configured to turn the deployment bar to lock each of the stabilization wings of the proximal stabilization wings and the distal stabilization wings into the deployed state.

According to another exemplary embodiment of the present invention, there is provided a stabilizer including a pair of proximal stabilization wings retracted within a first cavity of the distractor and configured to be deployed through a pair of proximal slots disposed on opposite sides of the proximal end of the central engagement groove; and a pair of distal stabilization wings retracted within a second cavity of the distractor and configured to be deployed through a pair of distal slots disposed on opposite sides of the distal end of the central engagement groove, wherein the pair of proximal stabilization wings and the pair of distal stabilization wings are coupled to the central engagement groove by a pressure mechanism such that the stabilization wings are deployed when the central engagement groove is pressurized by compression from the two spinous processes upon insertion therebetween.

According to another exemplary embodiment of the present invention, there is provided a stabilizer including a pair of proximal stabilization wings retracted within a first cavity of the distractor and configured to be deployed through a pair of proximal slots disposed on opposite sides of the proximal end of the central engagement groove, the proximal stabilization wings are balloon O-rings such that the proximal stabilization wings are deflated in a retracted state and inflated in a deployed state; a pair of distal stabilization wings retracted within a second cavity of the distractor and configured to be deployed through a pair of distal slots disposed on opposite sides of the distal end of the central engagement groove, the distal stabilization wings are balloon O-rings such that the distal stabilization wings are deflated in a retracted state and inflated in a deployed state; and a pump coupled to each of the proximal stabilization wings and distal stabilization wings to inflate the proximal stabilization wings and the distal stabilization wings to a deployed state.

According to another exemplary embodiment of the present invention, the insertion portion includes a pair of axial rectangular grooves, each disposed oppositely from each other, and the stabilizer includes a pair of side wings, each disposed within one of the pair of axial rectangular grooves and are configured to be congruent with a shape of the axial rectangular grooves and with a surface of the insertion portion in an undeployed state, the pair of side wings configured to be deployed outward from the axial rectangular grooves; a deployment means which deploys the pair of side wings from the axial rectangular grooves by pulling the side wings towards the proximal end of the central engagement groove such that such that the side wings open up from the axial rectangular grooves to a vertical position adjacent to the proximal end of the central engagement groove; and a pair of hinges, each hinge coupling the deployment means to a distal end of each of the side wings, enabling the side wings to open to a deployed state.

Furthermore, the insertion portion has a conical screw shape such that the surface of the insertion portion has screw-shaped (i.e., helical) grooves adapted to enable the distractor to be screwed into place between the two spinous processes. Thus, a surface of the side wings is configured to be congruent with the screw-shaped grooved surface of the insertion portion when the side wings are in an undeployed state.

In addition, the stabilizer may further include a stabilization base coupled to the distal end of the central engagement groove and which extends outward from the distractor and is adapted to inhibit the distractor from being inserted further between the two spinous processes.

According to another exemplary embodiment of the present invention, there is provided a method of performing interspinous distraction, the method includes inserting a distractor having a conical insertion portion and a central engagement groove between two spinous processes of vertebrae, the conical insertion portion adapted such that a gradual distraction between the two spinous processes occurs; inserting an insertion driver while coupled to the distractor, the insertion driver being detachably coupled to a rear portion of the distractor; implanting the distractor between the two spinous processes such that the two spinous processes rest in the central engagement groove between a proximal end and a distal end of the central engagement groove; deploying a stabilizer which is adapted to be deployed from within the distractor to secure the two spinous processes within the central engagement groove; and decoupling the insertion driver from the distractor and removing the insertion driver.

The method may also include locking the stabilizer in a deployed state.

The method may also include inserting a guide wire having a pointed tip between the two spinous processes, the guide wire configured to guide the inserting of the distractor and the inserting of the insertion driver between the two spinous processes while the insertion driver is coupled to the distractor, wherein the distractor and the insertion driver each have a guide channel disposed therein configured to accept the guide wire therein.

The inserting of the distractor may also include screwing the distractor into place between the two spinous processes, wherein the insertion portion has a conical screw shape such that a surface of the insertion portion has screw-shaped grooves adapted to enable the distractor to be screwed into place between the two spinous processes during the inserting of the distractor.

Furthermore, the insertion portion has an axis of distraction having a constant increasing angle that provides for constant distraction during the inserting of the distractor.

According to another exemplary embodiment of the present invention, there is provided a method of performing interspinous distraction, the method includes inserting a guide wire having a pointed tip between the two spinous processes; inserting a distractor having a conical insertion portion and a central engagement groove between two spinous processes of vertebrae, the conical insertion portion adapted such that a gradual distraction between the two spinous processes occurs; inserting an insertion driver while coupled to the distractor, the insertion driver being detachably coupled to a rear portion of the distractor; implanting the distractor between the two spinous processes such that the two spinous processes rest in the central engagement groove between a proximal end and a distal end of the central engagement groove; and decoupling the insertion driver from the distractor and removing the insertion driver, wherein the guide wire is configured to guide the inserting of the distractor and the inserting of the insertion driver between the two spinous processes while the insertion driver is coupled to the distractor, and the distractor and the insertion driver each have a guide channel disposed therein configured to accept the guide wire therein.

According to the above exemplary embodiments the conical interspinous device separates spinous process gradually and, in the central portion of the device, grooves allow for immediate stability. In some exemplary embodiments, the tip of the device, which is pointed, can be pulled back, thereby also locking the device into place.

Furthermore, according to the exemplary embodiments of present invention, there is provided a device having a solid nose housing (i.e., the distractor) permitting internal stabilization wing deployment devices to be internalized for a more minimally invasive device and technique.

Thus, a device which can be implanted between two spinous processes of the spine more easily and which involves less invasive procedures is provided which can be adapted for both fusion and non-fusion procedures.

BRIEF DESCRIPTION OF THE DRAWINGS

The above and other aspects of the present invention will become more apparent from the following description of exemplary embodiments, taken in conjunction with the accompanying drawings of which.

Throughout the drawings, the same drawing reference numerals will be understood to refer to the same elements, features, and structures.

DETAILED DESCRIPTION OF THE EXEMPLARY EMBODIMENTS

The matters defined in the description such as a detailed construction and elements are provided to assist in a comprehensive understanding of the embodiment of the invention and are merely exemplary. Accordingly, those of ordinary skill in the art will recognize that various changes and modifications of the embodiment described herein can be made without departing from the scope and spirit of the invention. Also, descriptions of well-known functions and constructions are omitted for clarity and conciseness.

The device is composed of a device which has a pointed conical shape with embedded screw-shaped (i.e., helical) grooves that permit the passage of the device between the spinous processes of the human spine. The device is designed to be positioned between two spinous processes. It is placed through the interspinous ligament and below the supra-spinous ligament. The grooved conical surface permits the device to be screwed into place in a percutaneous or traditional open surgery. The device is secured between the spinous processes due to a deeper central engagement groove as well as by mechanisms to be described whereby the end(s) of the device are further stabilized. Due to its position within the interspinous ligament and below the supra-spinous ligament, further stability is obtained.

Furthermore, due to its geometric shape, the device gradually spreads the spinous processes apart. By spreading the spinous processes apart, the volume of the spinal canal and vertebral foramen are increased thereby decompressing the spine in cases of spinal stenosis.

A unique feature of this procedure is that there is no required instrumentation to place the final device into its final position except for a device holding tool (i.e., an insertion driver). Provisional dilation of the spinous processes can be performed if so desired with solid dilators also of conical screw or a smooth semi-conical shape. The depth and pitch and other parameters of a screw configuration can be modified to provide faster insertion, more stable insertion, and positioning of the implant. The central groove may be deeper and broader to accept the spinous process anatomic region in a stable and consistent manner. The device can be either solid or cannulated.

Figure 1:
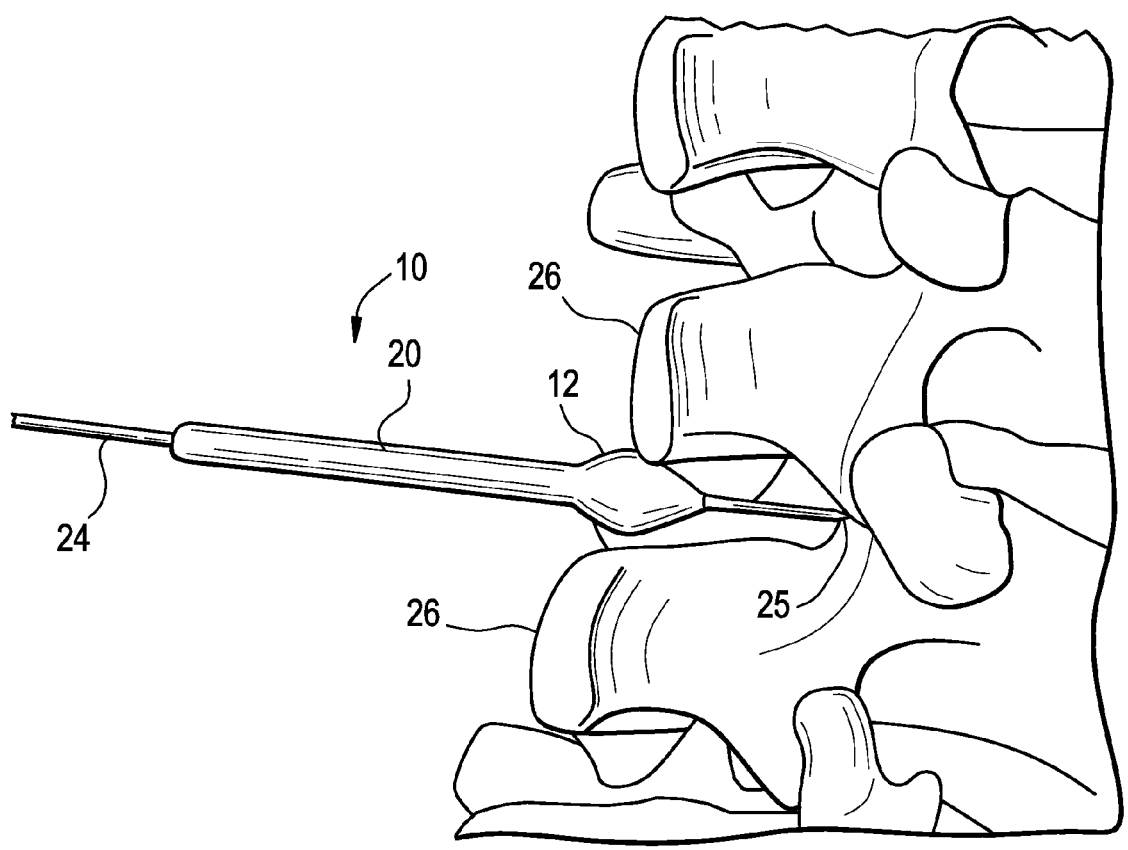
FIG. 1 illustrates an interspinous apparatus according to an exemplary embodiment of the present invention.

FIG. 1 illustrates a high level drawing of an interspinous apparatus 10 according to an exemplary embodiment of the present invention. The interspinous apparatus 10 includes a distractor 12, an insertion driver 20, and a guide wire 24 having a pointed tip 25. The distractor 12 has a conical shape which is adapted to enable passage of the distractor 12 between two spinous processes 26 of vertebrae such that a gradual distraction between the two spinous processes 26 occurs. Each of the distractor 12 and the insertion driver 20 have a guide channel which extends through an entire central portion therein configured to accept the guide wire 24 therein. The pointed tip 25 of the guide wire 24 permits an easier insertion of the guide wire 24 between the two spinous processes 26. The guide wire 24 is inserted between the two spinous processes 26 in order to guide the insertion of the distractor 12, detachably coupled to the insertion driver 20, between the two spinous processes 26.

The distractor 12 has a conical shape which is adapted to enable passage of the distractor 12 between two spinous processes 26 that a gradual distraction between the two spinous processes 26 occurs. Due to the conical shape of the distractor 12, the distractor 12 has an axis of distraction, to be described later, having a constant increasing angle that provides for constant distraction.

The distractor 12 can be composed of any solid or semi solid material including but not limited to poly-ether-ether-ketone (PEEK), titanium, stainless steel, or bone. In addition, the distractor 12 may be composed of but not limited to hydroxyapatite, bone substitutes, a combination of hydroxyapatite and bone cement, CORTOSS, or the like. If the distractor 12 is composed of any material besides bone, motion is preserved due to the rolling effect of the cone in extension and flexion. If the distractor 12 is composed of bone, the device can be used to induce fusion. Thus, the device could also be used to fuse spines depending on what material it is made of.

If less motion is so desired, the central engagement groove 14 can be partially flattened thereby decreasing the rolling effect of the device providing more stability.

If the distractor 12 is composed of bone, the distractor 12 may be used to treat patients who require fusion with or without decompression of the spinal canal and foramen. In patients who do not require a fusion, materials such as PEEK, steel, titanium, or other alloys could be utilized.

Figure 2A:
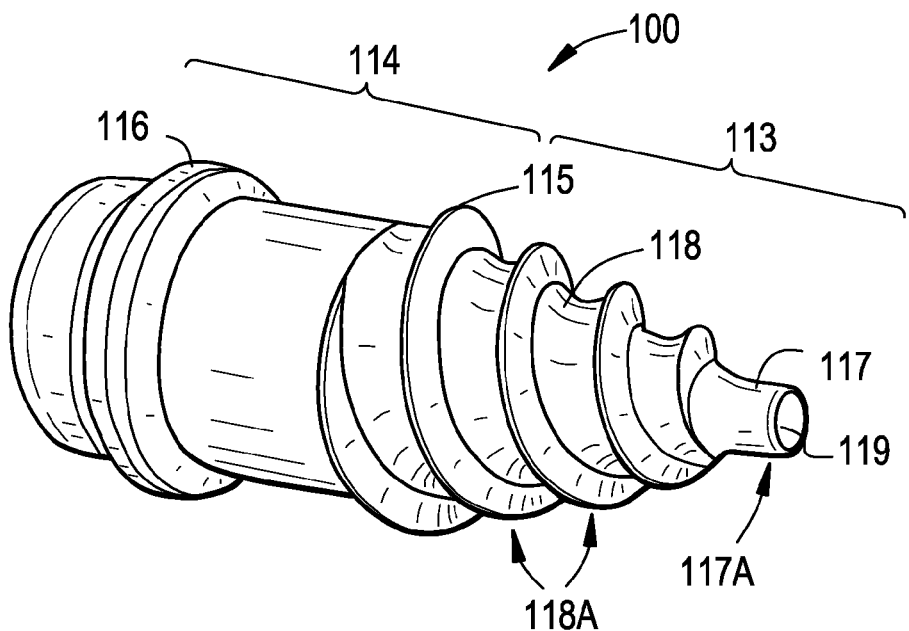
FIG. 2A illustrates a dilator according to an exemplary embodiment of the present invention.
Figure 2B:
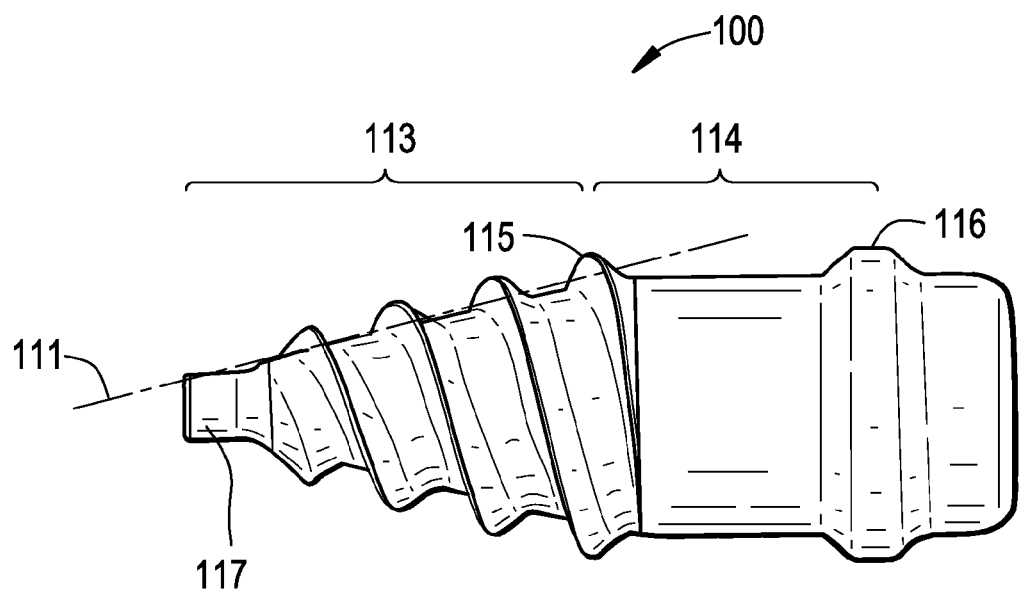
FIG. 2B illustrates another view of the dilator shown in FIG 2A.

FIGS. 2A and 2B illustrate a solid dilator 100 that is used before the distractor 12 according to an exemplary embodiment of the present invention. The dilator 100 includes an insertion portion 113 and a central engagement groove 114 having a proximal end 115 and a distal end 116.

The insertion portion 113 has a conical shape which tapers from the proximal end 115 of the central engagement groove 114 to a tip 117 and is adapted to enable passage of the dilator 100 between the two spinous processes 26 such that a gradual distraction between the two spinous processes 26 occurs. The insertion portion 113 has embedded screw-shaped (i.e., helical) grooves 118 which permits the device to be screwed into place in a percutaneous or traditional open surgery. The grooves 118 include sharp edges 118A that are configured to incise through a patient's interspinous ligament (not shown). Because the sharp edges 118A are also screw-shaped (i.e., helical), the edges 118A can serially dilates/spread the interspinous ligament apart. Moreover, the concave grooves 118 dilator keep the interspinous ligament distracted while the next edge 118A incises the ligament. The insertion portion 113 an axis of distraction 111 having a constant increasing angle that provides for constant distraction. The tip 117 of the insertion portion 113 is ungrooved to allow for ease of initial insertions, but may be grooved. Furthermore, the tip 119 is hollow, showing a portion of the guide channel 119 which extends through the entire central portion of the distractor 112 for accepting the guide wire 124 therein. The tip 119 also includes a sharp edge 119A this is configured to cut through the patient's interspinous ligament.

The central engagement groove 114 is adapted to secure the dilator 100 between the two spinous processes 26 such that the two spinous processes 26 rest in the central engagement groove 14 between the proximal end 115 and the distal end 116.

Figure 3:
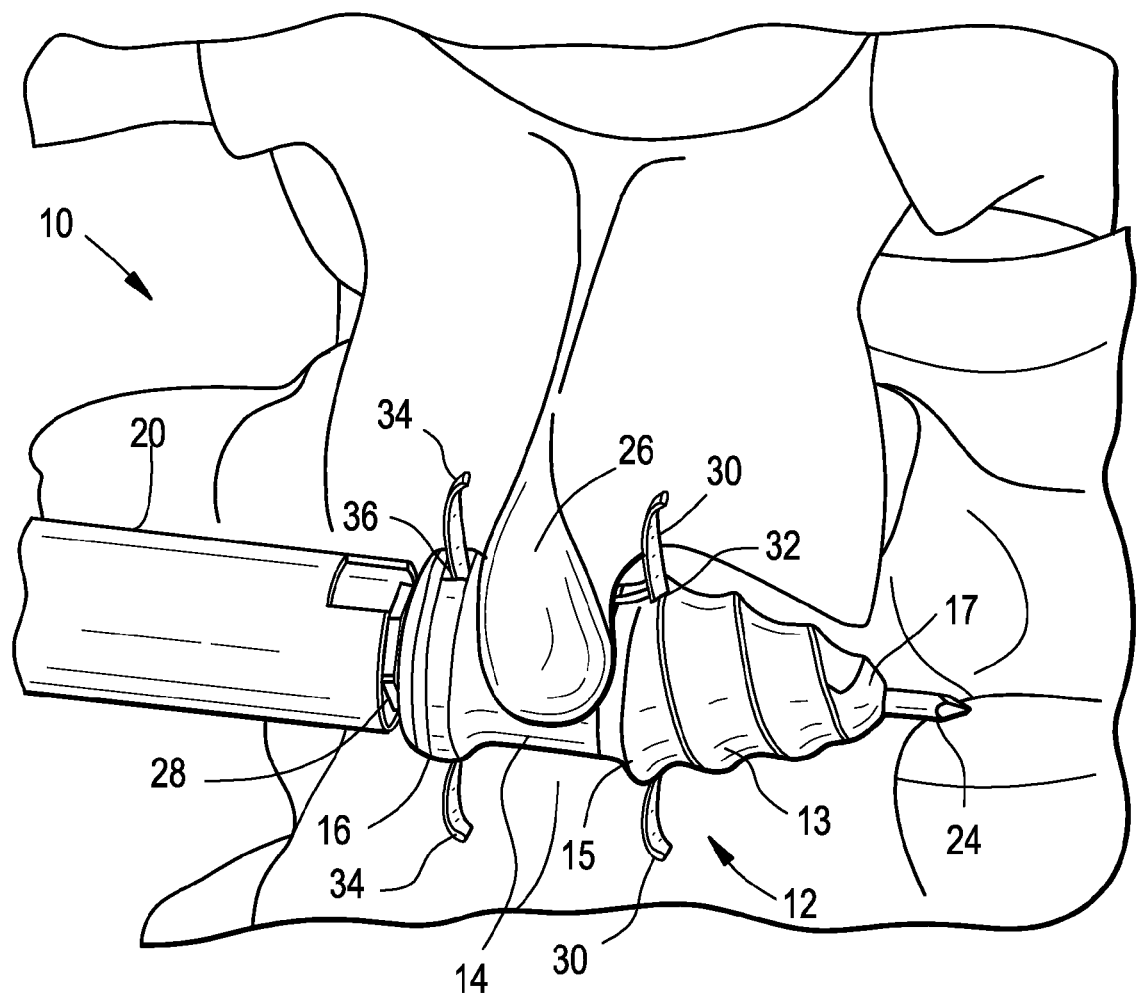
FIG. 3 illustrates an interspinous apparatus according to an exemplary embodiment of the present invention.

FIG. 3 illustrates an interspinous apparatus 10 according to another exemplary embodiment of the present invention. The distractor is inserted after the dilator 100 is removed and includes an insertion portion 13 and a central engagement groove 14 having a proximal end 15 and a distal end 16.

Like the dilator 100, the insertion portion 13 has a conical shape which tapers from the proximal end 15 of the central engagement groove 14 to a tip 17 and is adapted to enable passage of the distractor 12 between the two spinous processes 26 such that a gradual distraction between the two spinous processes 26 occurs. The insertion portion 13 has embedded screw-shaped (i.e., helical) grooves 18 which permits the device to be screwed into place in a percutaneous or traditional open surgery. The insertion portion 13 an axis of distraction 11 having a constant increasing angle that provides for constant distraction. The tip 17 of the insertion portion 13 is ungrooved to allow for ease of initial insertions, but may be grooved. Furthermore, the tip 19 is hollow, showing a portion of the guide channel 19 which extends through the entire central portion of the distractor 12 for accepting the guide wire 24 therein.

The central engagement groove 14 is adapted to secure the distractor 12 between the two spinous processes 26 such that the two spinous processes 26 rest in the central engagement groove 14 between the proximal end 15 and the distal end 16.

The interspinous apparatus 10 includes the distractor 12 having a rear portion 28 detachably coupled to the insertion driver 20, and the guide wire 24. The insertion portion 13, as shown, has a tip 17 which is grooved. In contrast to the dilator 100, the distractor 12 includes a pair of proximal stabilization wings 30 retracted within a first cavity (not shown) of the distractor 12 and configured to be deployed through a pair of proximal slots 32 disposed on opposite sides of the proximal end 15 of the central engagement groove 14. The stabilization wings 30 are deployed after the spinous processes 26 are secured in the central engagement groove 14 to inhibit the distractor 12 from reversing out from between the two spinous processes 26.

The distractor may also include a pair of distal stabilization wings 34 retracted within a second cavity (not shown) of the distractor 12 and configured to be deployed through a pair of distal slots 36 disposed on opposite sides of the distal end 16 of the central engagement groove 14. The stabilization wings 34 are deployed after the spinous processes 26 are secured in the central engagement groove 14 to inhibit the distractor from being inserted further between the two spinous processes 26. Thus, the proximal stabilization wings 30 and the distal stabilization wings 34 stabilize the two spinous processes 26 within the central engagement groove 14.

Figure 4:
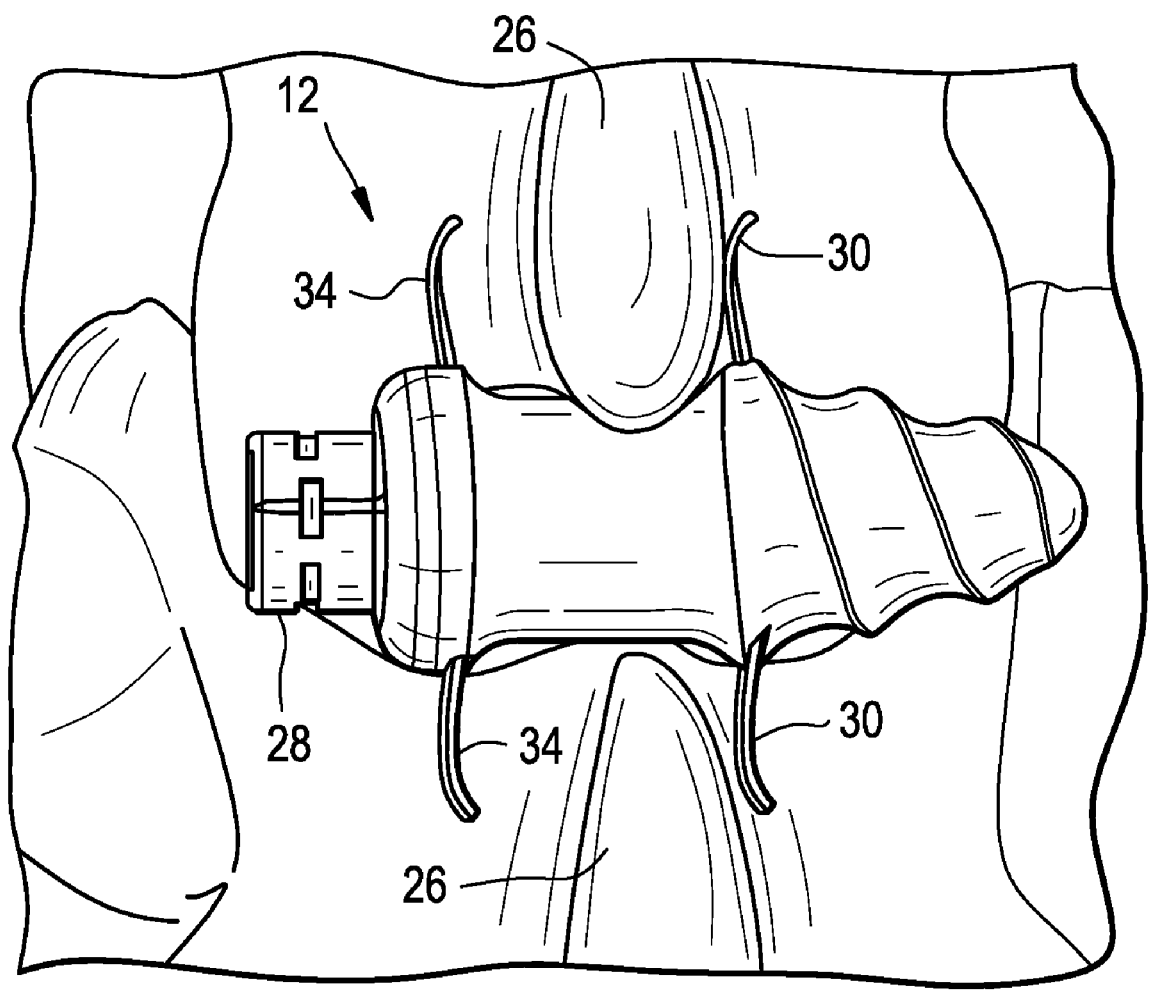
FIG. 4 illustrates an interspinous apparatus according to the exemplary embodiment of the present invention.

FIG. 4 illustrates an interspinous apparatus 10 having the insertion driver 20 decoupled from the rear portion 28 of the distractor 12 and the guide wire 24 removed from the distractor 12. Thus, the distractor 12 is shown implanted between the two spinous processes 26 and having the proximal stabilization wings 30 and the distal stabilization wings 34 deployed from within the distractor 12.

In addition, a circular ring can be slipped over either end of the device and tightened thereby providing stability to the implant (not shown).

Figure 5:
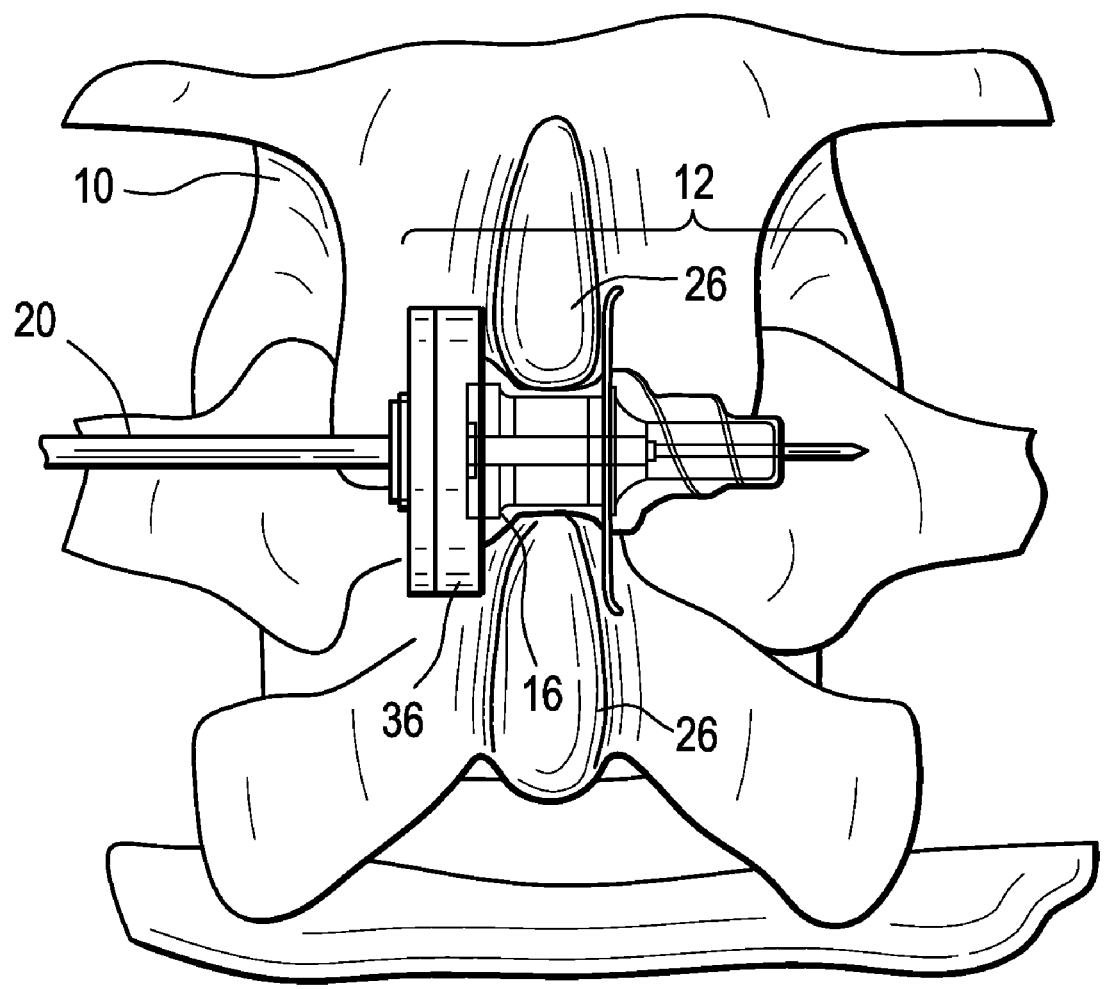
FIG. 5 illustrates an interspinous apparatus according to another exemplary embodiment of the present invention.

FIG. 5 illustrates an interspinous apparatus 10 according to another exemplary embodiment of the present invention. In particular, the distractor 12 includes a stabilization base 36 in the alternative to the distal stabilization wings 34. The stabilization base 36 is coupled to the distal end 16 of the central engagement groove 14 and which extends outward from the distractor 12. The stabilization base 36, much like the distal stabilization wings 34, is adapted to inhibit the distractor from being inserted further between the two spinous processes 26.

Figure 6A:
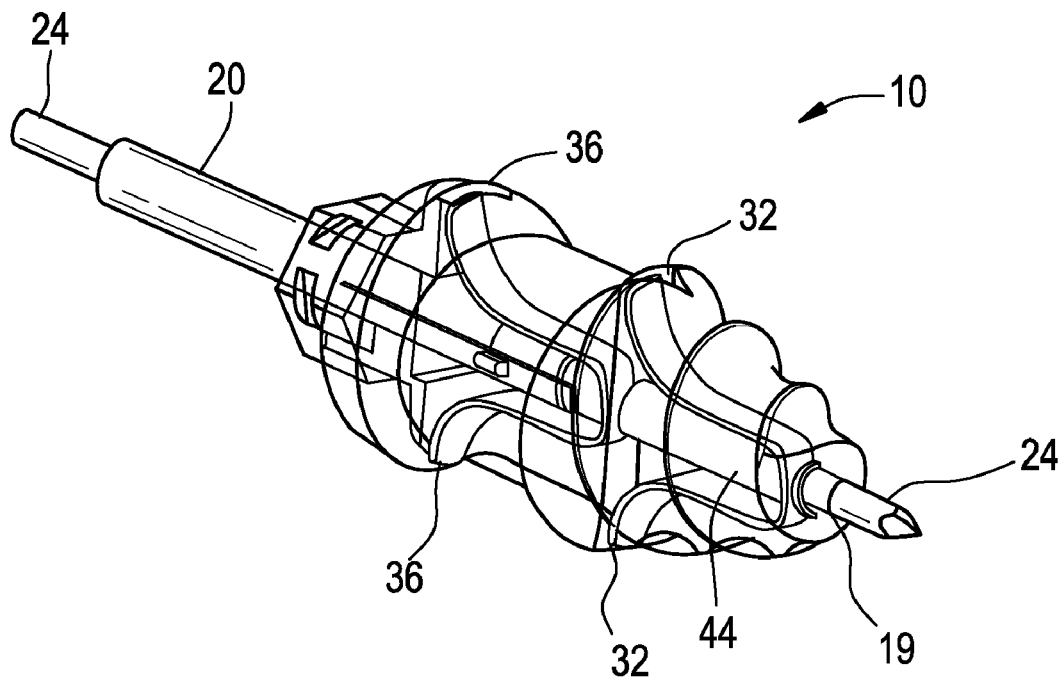
FIG. 6A illustrates an interspinous apparatus having stabilizers in a retracted state according to another exemplary embodiment of the present invention.
Figure 6B:
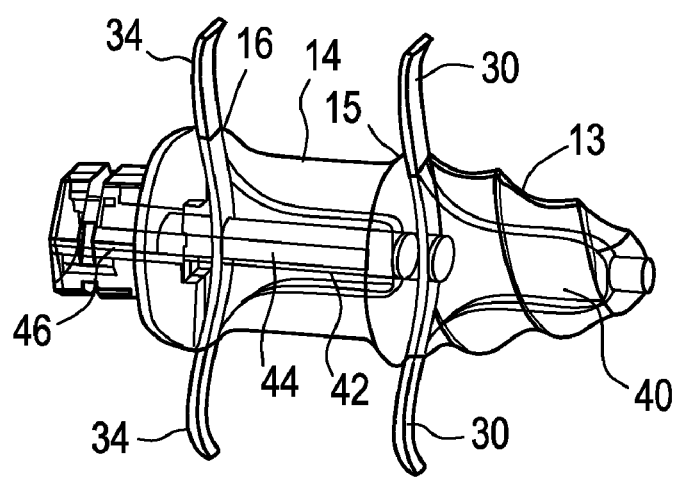
FIG. 6B illustrates an interspinous apparatus having stabilizers in a deployed state according to the exemplary embodiment of the present invention shown in FIG. 6A.

FIGS. 6A and 6B illustrate an interspinous apparatus having stabilizers 30 and 34 in a retracted state and in a deployed state, respectively, according to another exemplary embodiment of the present invention.

The guide wire 24 is disposed within the guide channel 19, which extends through the entire central portion of the distractor 12 and the insertion driver 20. Each guide channel 19 of the distractor 12 and the insertion driver 20 is in alignment with each other.

The distractor 12 includes the pair of proximal stabilization wings 30 retracted within a first cavity 40 of the distractor 12. The proximal stabilization wings 30 are configured to be deployed through the pair of proximal slots 32 disposed on opposite sides of the proximal end 15 of the central engagement groove 14. In addition, the distractor 12 includes the pair of distal stabilization wings 34 retracted within a second cavity 42 of the distractor 12. The distal stabilization wings 34 are configured to be deployed through the pair of distal slots 36 disposed on opposite sides of the distal end 16 of the central engagement groove 14.

The distractor 12 includes a deployment bar 44 disposed therein and detachably coupled to the insertion driver 20. The deployment bar 44 is also coupled to each stabilization wing of the proximal stabilization wings 30 and the distal stabilization wings 34. The deployment bar 44 is disposed within the guide channel 19 of the distractor 12 and is configured to be slidably switched between an extended position (as shown in FIG. 6A) and a retracted position (as shown in FIG. 6B).

Thus, when the deployment bar 44 is in the extended position, the deployment bar 44 maintains the proximal stabilization wings 30 and the distal stabilization wings 34 in a retracted state. On the other hand, when deployment bar 44 is in the retracted position, the deployment bar 44 releases the proximal stabilization wings 30 and the distal stabilization wings 34 to a deployed state. The deployment bar 44 is slidably switched between the extended position and the retracted position by moving the portion of the insertion driver 20 that is detachably coupled to the deployment bar 44 in and out of the distractor 12.

When the deployment bar 44 is an a retracted position and the stabilization wings 30 and 34 are in the deployed state, the stabilization wings 30 and 34 may be locked into their deployed position by a lock configured to engage with the deployment bar 44. For example, the portion of the insertion driver 20 that is detachably coupled to the deployment bar 44 may be rotated, and in turn rotating the deployment bar 44 within the distractor 12 to a locked position. Once in a locked state, the insertion driver 20 can be decoupled from the deployment bar 44 and removed from the guide wire 24.

Figure 7:
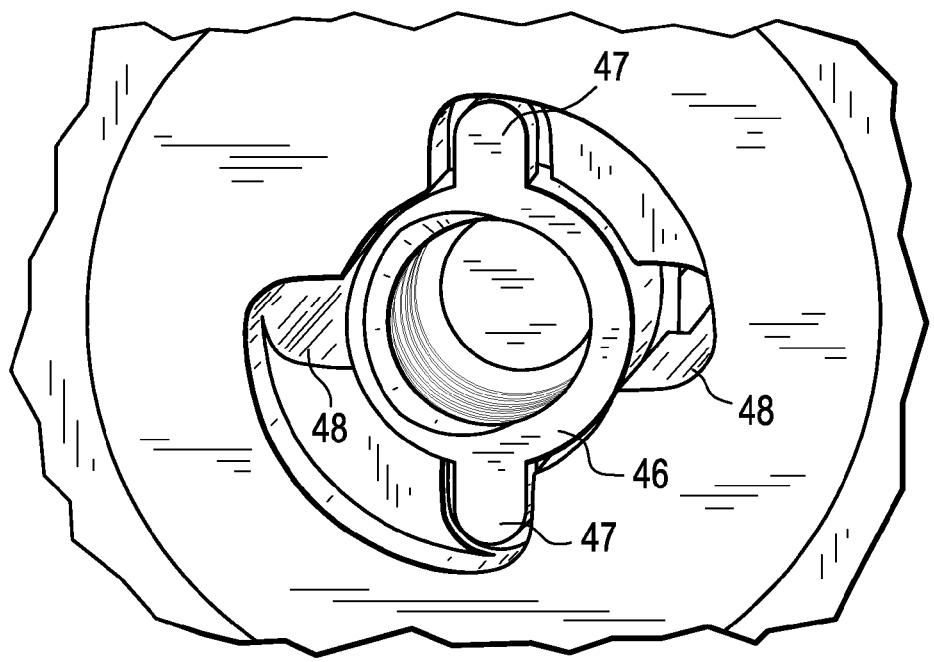
FIG. 7 illustrates a locking mechanism according to an exemplary embodiment of the present invention.

FIG. 7 illustrates a locking mechanism according to an exemplary embodiment of the present invention. In particular, a rear portion 46 (as shown in FIGS. 6A and 6B) of the deployment bar 44 has interlocking members 47 which can be rotated clockwise to engage locking slots 48 to lock the deployment bar 44 into place, and thereby, locking the stabilization wings 30 and 34 in the deployed state.

Figure 8:
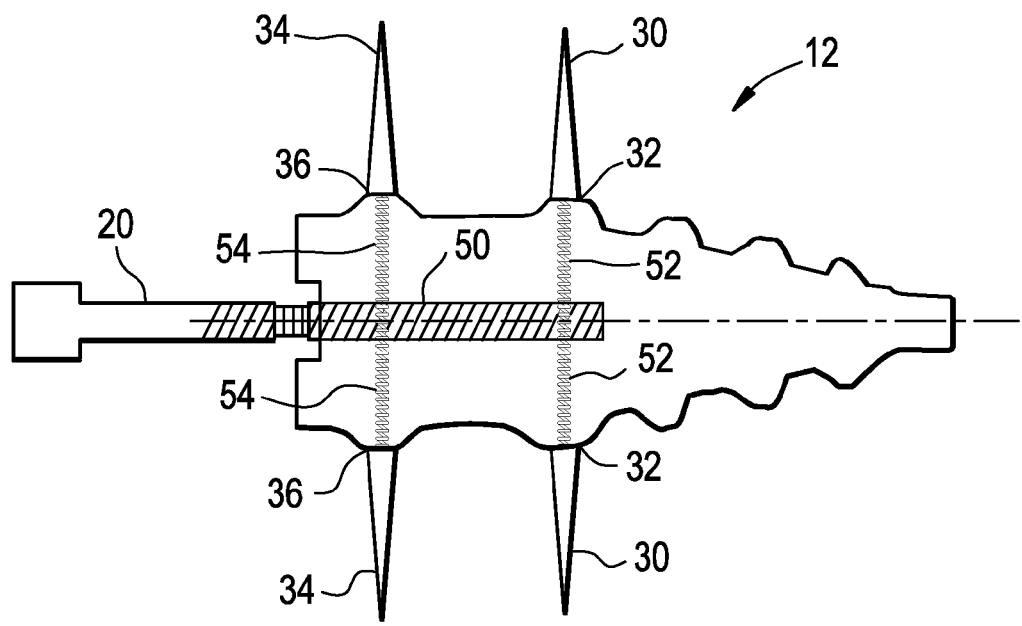
FIG. 8 illustrates an interspinous apparatus according to another exemplary embodiment of the present invention.

FIG. 8 illustrates an interspinous apparatus according to another exemplary embodiment of the present invention. In particular, FIG. 8 illustrates an alternative mechanism for deploying the proximal stabilization wings 30 and the distal stabilization wings 34. The distractor 12 includes an insertion screw driver 50 disposed within the guide channel of the distractor, coupled to the insertion driver 20 and configured to engage a first pair of gears 52 and a second pair of gears 54. Each gear 52 and 54 is mechanically coupled to a respective stabilization wing 30 and 34. Thus, when the insertion driver 20 is turned, the insertion screw driver 50 is turned within the distractor 12 and engages with the first pair of gears 52 to deploy the pair of proximal stabilization wings 30 from the proximal slots 32 and engages with the second pair of gears 54 to deploy the pair of distal stabilization wings 34 from the distal slots 36.

Figure 9:
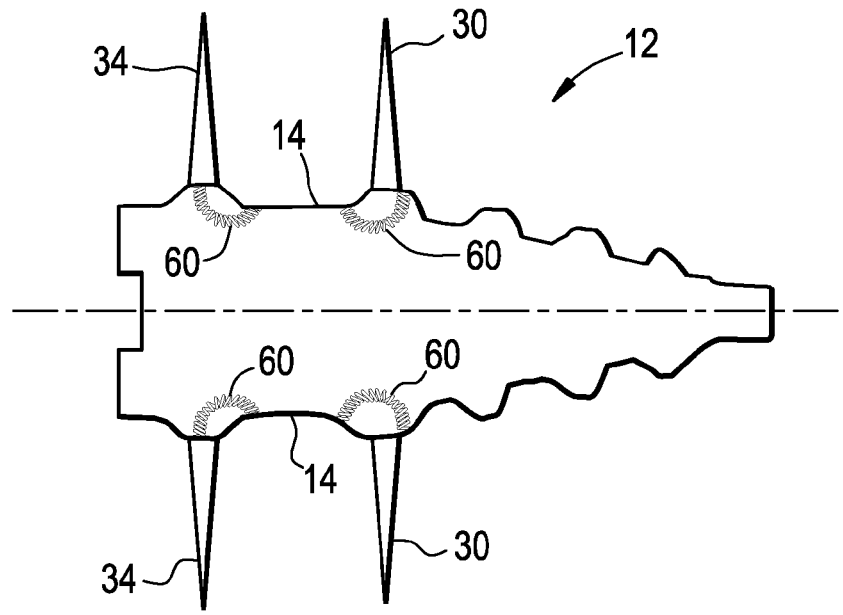
FIG. 9 illustrates an interspinous apparatus according to another exemplary embodiment of the present invention.

FIG. 9 illustrates an interspinous apparatus according to another exemplary embodiment of the present invention. In particular, FIG. 9 illustrates an alternative mechanism for deploying the proximal stabilization wings 30 and the distal stabilization wings 34.

Each stabilization wing of the pair of proximal stabilization wings 30 and the pair of distal stabilization wings 34 are coupled to the central engagement groove 14 by a pressure mechanism 60 such that the stabilization wings 30 and 34 are deployed when the central engagement groove 14 is pressurized by compression from the two spinous processes 26 upon insertion therebetween. The pressure on the central engagement groove 14 deploys the stabilization wings 30 and 34 from within the distractor 12.

Figure 10:
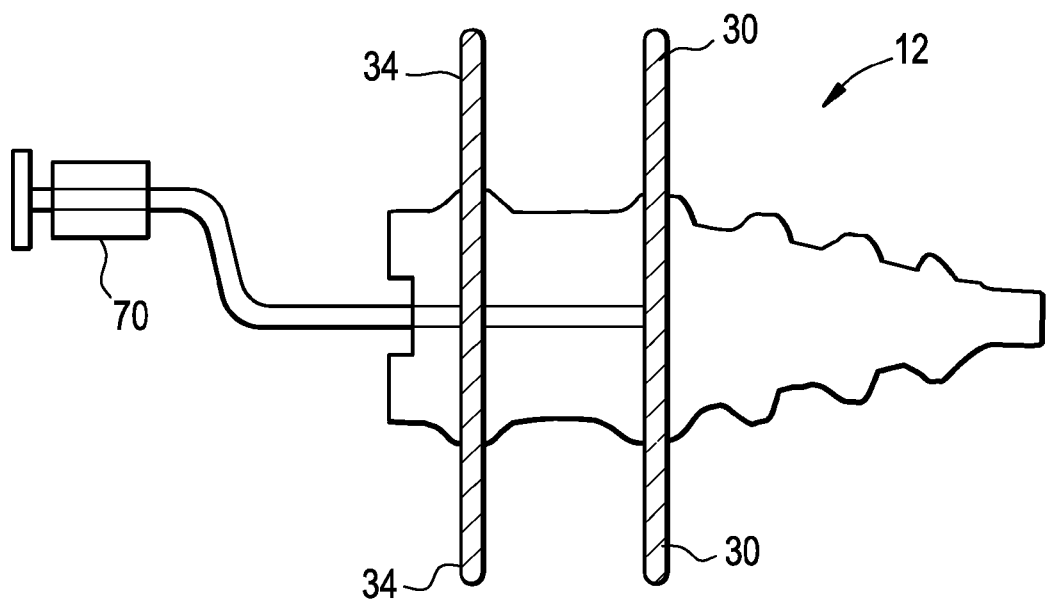
FIG. 10 illustrates an interspinous apparatus according to another exemplary embodiment of the present invention.

FIG. 10 illustrates an interspinous apparatus according to another exemplary embodiment of the present invention. In particular, FIG. 10 illustrates an alternative mechanism for deploying the proximal stabilization wings 30 and the distal stabilization wings 34.

The proximal stabilization wings 30 and distal stabilization wings are balloon O-rings such that the stabilization wings 30 and 34 are deflated in a retracted state and inflated in a deployed state.

A pump 70 coupled to each of the proximal stabilization wings 30 and distal stabilization wings 34 is used to inflate the proximal stabilization wings 30 and the distal stabilization wings to a deployed state 34. The O-rings can be inflated with either a gas or a liquid to stabilize the implant.

Figure 11A:
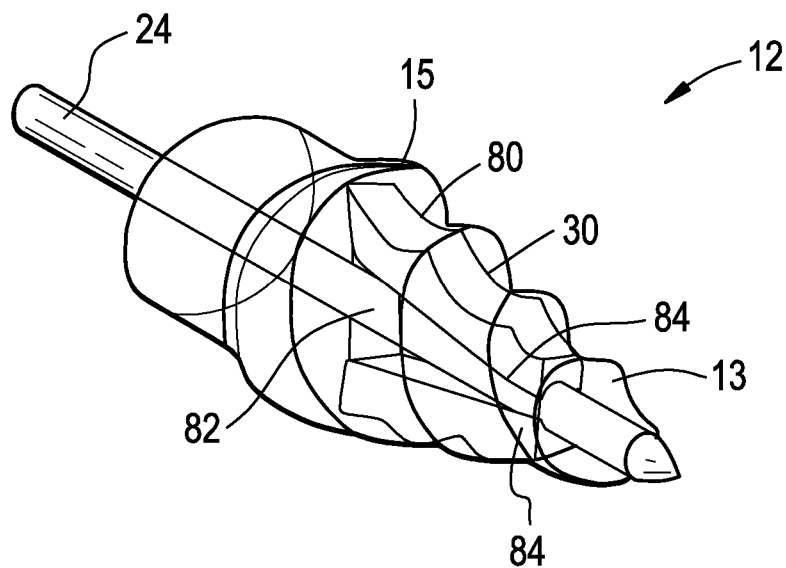
FIGS. 11A and 11B illustrate an interspinous apparatus according to another exemplary embodiment of the present invention.
Figure 11B:
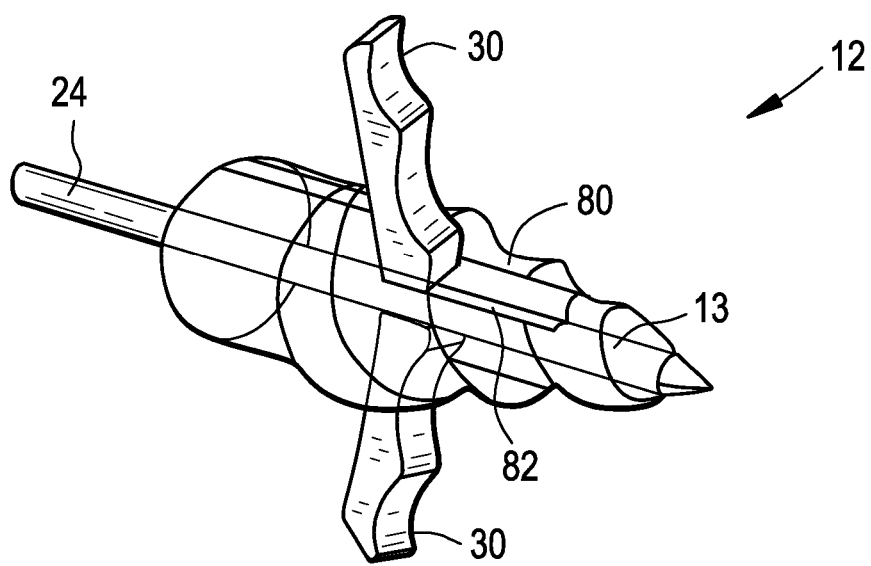

FIGS. 11A and 11B illustrate an interspinous apparatus according to another exemplary embodiment of the present invention. In particular, FIGS. 11A and 11B illustrate an alternative mechanism for deploying the proximal stabilization wings 30. FIGS. 11A and 11B illustrate an interspinous apparatus having stabilizers 30 in a retracted state and in a deployed state, respectively, according to another exemplary embodiment of the present invention.

The insertion portion 13 includes a pair of axial rectangular grooves 80, each disposed oppositely from each other. Within the pair of axial rectangular grooves 80 is disposed the pair of proximal stabilization wings 30 or side wings. Each proximal stabilization wing 30 is disposed within one of the pair of axial rectangular grooves 80. Furthermore, the proximal stabilization wings 30 are configured to be congruent with a shape of the axial rectangular grooves 80 and with a surface of the insertion portion 13 in an undeployed state as shown in FIG. 11A. Thus, if the insertion portion 13 has a conical screw shape such that the surface of the insertion portion has screw-shaped grooves 18, a surfaces of the proximal stabilization wings 30 also have grooves to be congruent the grooved surface of the insertion portion 13. This enables the distractor 12 to be screwed into place between the two spinous processes 26 when the proximal stabilization wings 30 are undeployed.

The proximal stabilization wings 30 are also configured to be deployed outward from the axial rectangular grooves 80 as shown in FIG. 11B. A deployment means 82 deploys the pair of proximal stabilization wings 30 from the axial rectangular grooves 80 by pulling the stabilization wings 30 towards the proximal end 15 of the central engagement groove 14 such that such that the stabilization wings 30 open up from the axial rectangular grooves 80 to a vertical position adjacent to the proximal end 15 of the central engagement groove 14. The stabilization wings 30 are coupled to the deployment means 82 by a pair of hinges 84, enabling the stabilization wings 30 to open to a deployed state.

The distractor 12 may also include the stabilization base 36 similar to that shown in FIG. 5.

Figure 12A:
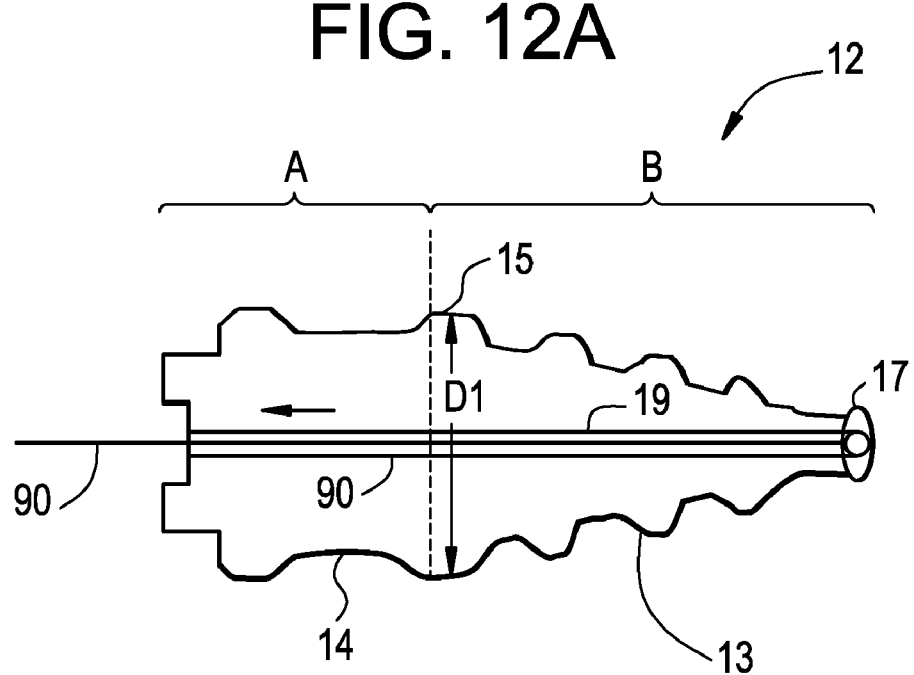
FIGS. 12A and 12B illustrate an interspinous apparatus according to another exemplary embodiment of the present invention.
Figure 12B:
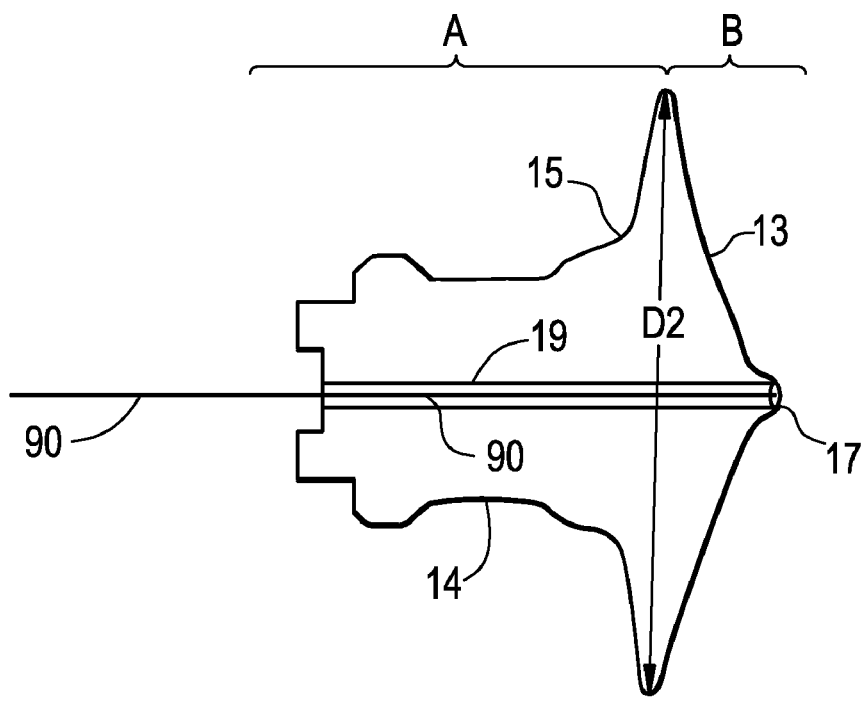

FIGS. 12A and 12B illustrate an interspinous apparatus according to another exemplary embodiment of the present invention. In particular, FIGS. 12A and 12B illustrate an alternative mechanism for deploying a stabilizer.

The distractor 12, and more particularly, the insertion portion 13 may be composed of differing materials to permit for a collapsing umbrella stabilizing tip to be deployed. The insertion portion 13 is made of flexible material having a first diameter D1 at the proximal end 15 of the central engagement groove 14. The insertion portion 13 is configured to collapse towards the proximal end of the central engagement groove such that the insertion portion 13 is compressed into a shape having a second diameter D2 at the proximal end 15 of the central engagement groove 14 larger than the first diameter D1 after the distractor 12 is implanted to inhibit the distractor 12 from reversing out from between the two spinous processes 26.

The distractor 12 includes a wire 90 fed through the guide channel 19 and connected to the tip 17 of the insertion portion 13. The tip 17 of the insertion portion 13 is adapted to be pulled towards the central engagement groove 14 upon pulling of the wire 90 to collapse the insertion portion 13. Thus, the length of portion B collapses, while the length of portion A remains constant and rigid.

The distractor 12 may also include the stabilization base 36 similar to that shown in FIG. 5.

Further, it would be understood that the stabilization base 36 as described in FIG. 5 could be implemented in any of the above exemplary embodiments.

Figure 13A:
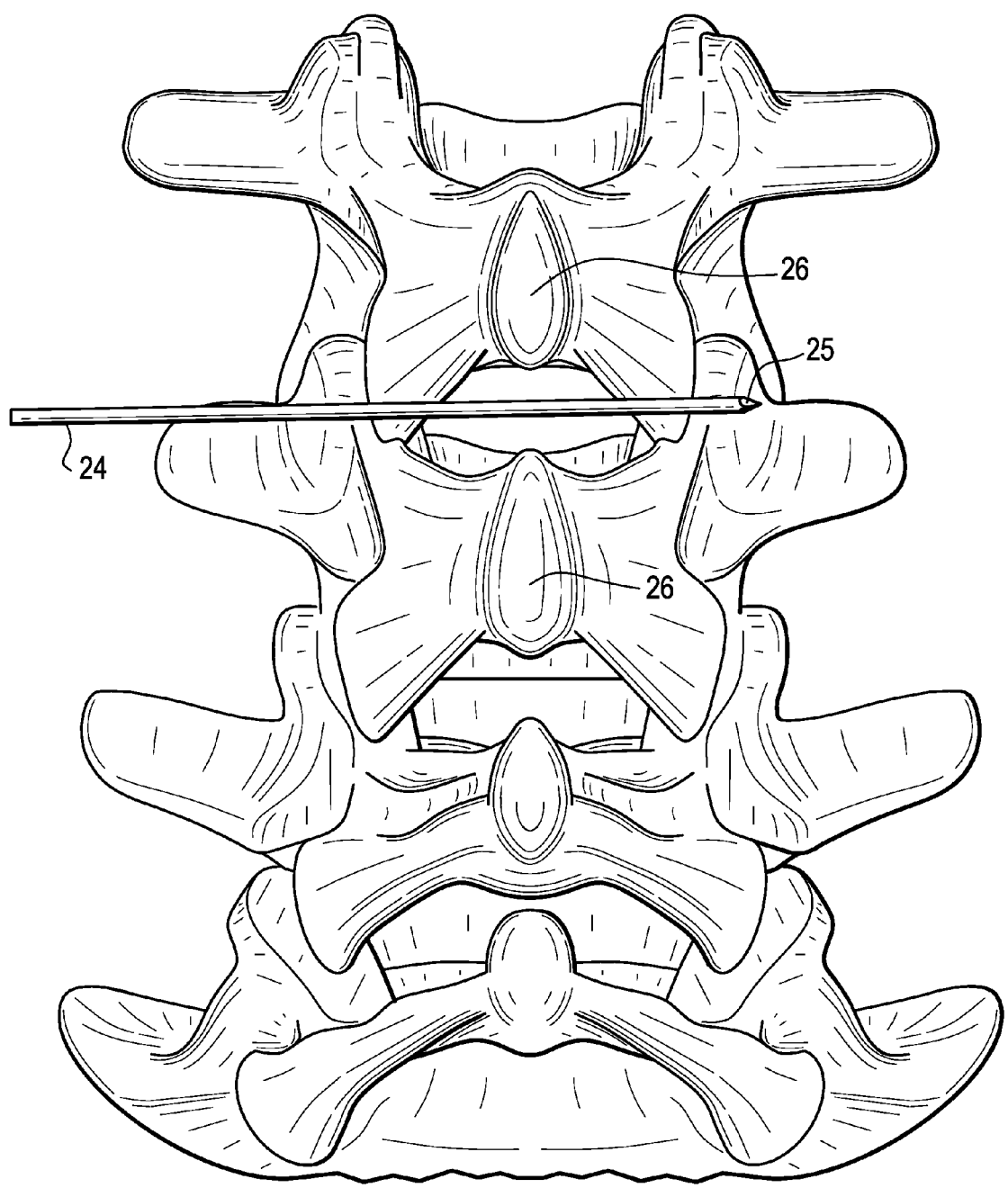
FIGS. 13A-13I illustrate a method of performing interspinous distraction according to an exemplary embodiment of the present invention.

FIGS. 13A-13H illustrate a method of performing interspinous distraction according to an exemplary embodiment of the present invention. The method includes inserting a guide wire 24 having a pointed tip 25 between the two spinous processes 26 (FIG. 13A). The guide wire 24 is configured to guide the insertion of the distractor 12 and the inserting of the insertion driver 20 between the two spinous processes 26 while the insertion driver 20 is coupled to the distractor 12.

The distractor 12 and the insertion driver 20 each have a guide channel 19 disposed therein configured to accept the guide wire 24 therein.

Figure 13B:
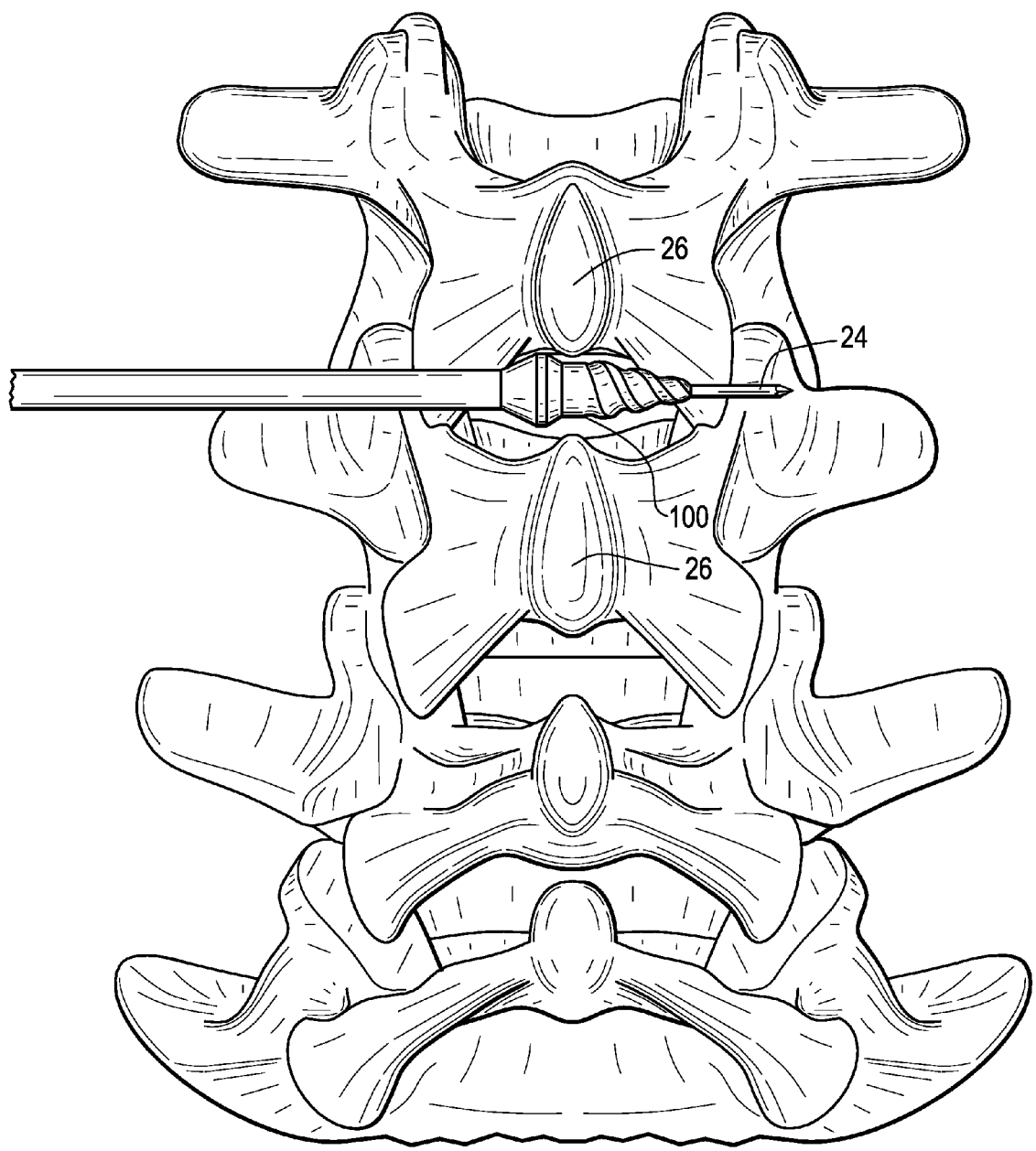
Figure 13C:
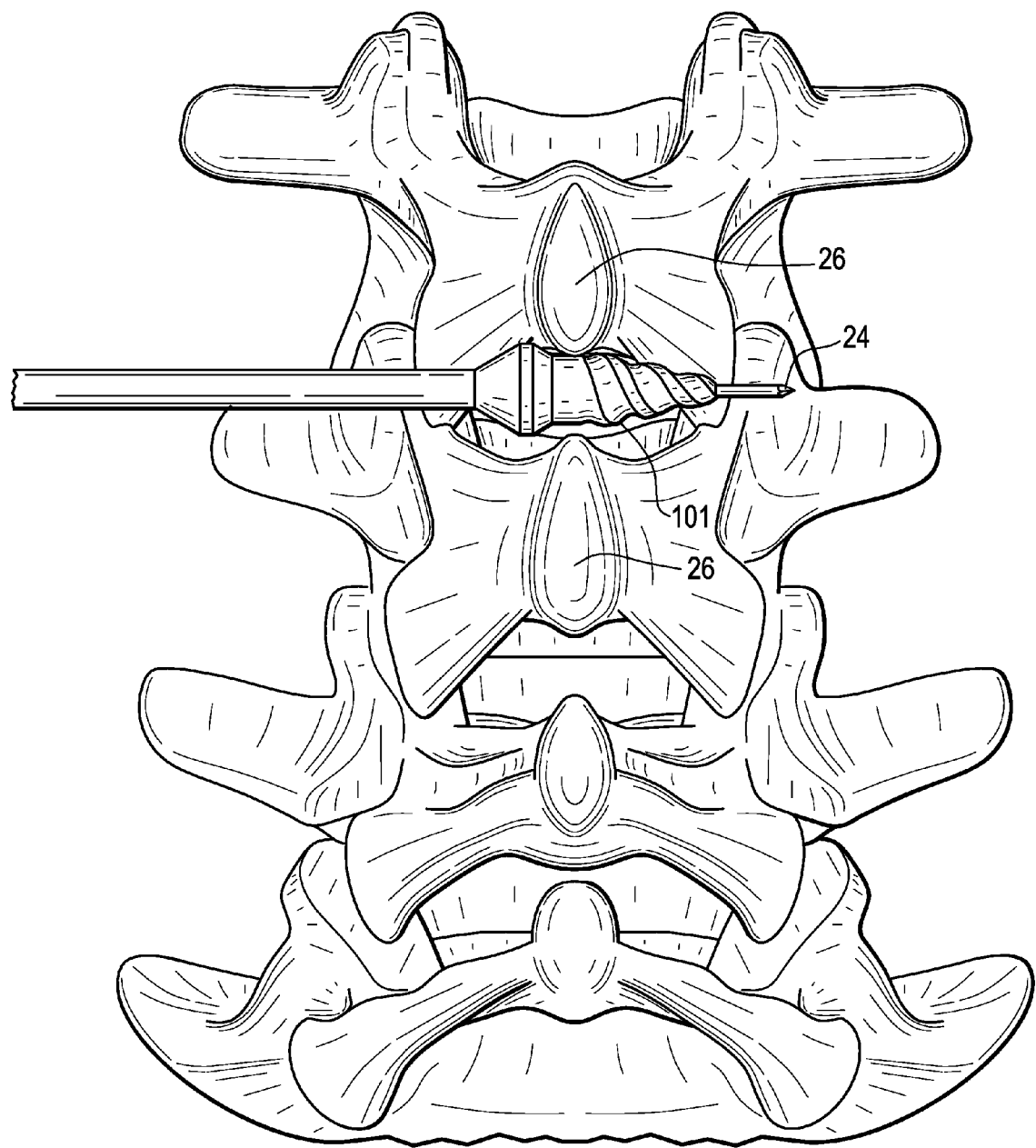

Provisional dilation of the spinous processes 26 is performed with cannulated conical screw or smooth semi conical shape dilators 100 and 100, as shown in FIGS. 13B and 13C. During provisional dilation, the first dilator 100 is inserted via the guide wire 24 and cuts through the interspinous ligament (not shown) using the sharp edges 117A, 118A. The dilator 100 distracts the spinous processes 26 if the dilator 100 comes into contact with the spinous processes 26. Then, the first dilator 100 is removed.

If the first dilator 100 does not contact the spinous processes 26, a second dilator 101 is inserted via the guide wire 24. The second dilator 101 is larger than the first dilator 100 and also cuts through the interspinous ligament. If necessary, several dilators 100, 101, etc. can be used until one of the dilators contacts the spinous processes 26. The dilators can have slightly increasing outer diameters. For example, a 6 mm, an 8 mm, a 10 mm, a 12 mm, and a 14 mm dilator can be used.

Contact between the dilator and the spinous processes 26 can be felt due to the tension provided between the spinous processes 26 by the super spinous ligament (not shown). Once the proper size is determined by the dilator, a distractor of an appropriate size can be selected.

Figure 13D:
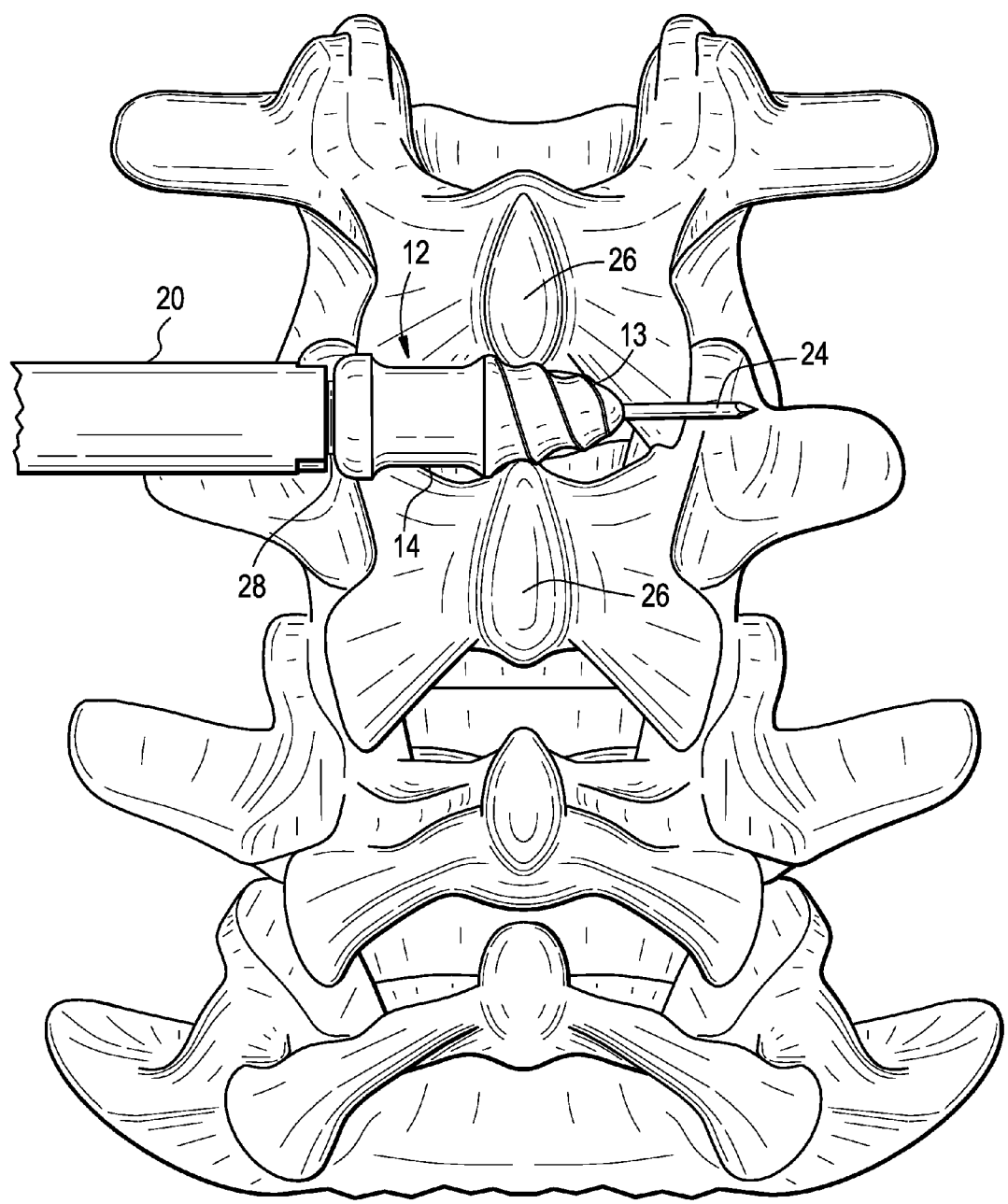

The method further includes inserting the distractor 12 having a conical insertion portion 13 and a central engagement groove 14 between the two spinous processes 26 (FIG. 13D). The conical insertion portion 13 is adapted such that a gradual distraction between the two spinous processes occurs 26. The insertion drive 20 acts as a device holding tool for inserting the distractor 12 between the spinous processes 26. Thus, FIG. 13D also illustrates inserting the insertion driver 20 while coupled to the distractor 12, the insertion driver 20 being detachably coupled to a rear portion 28 of the distractor 12.

Figure 13E:
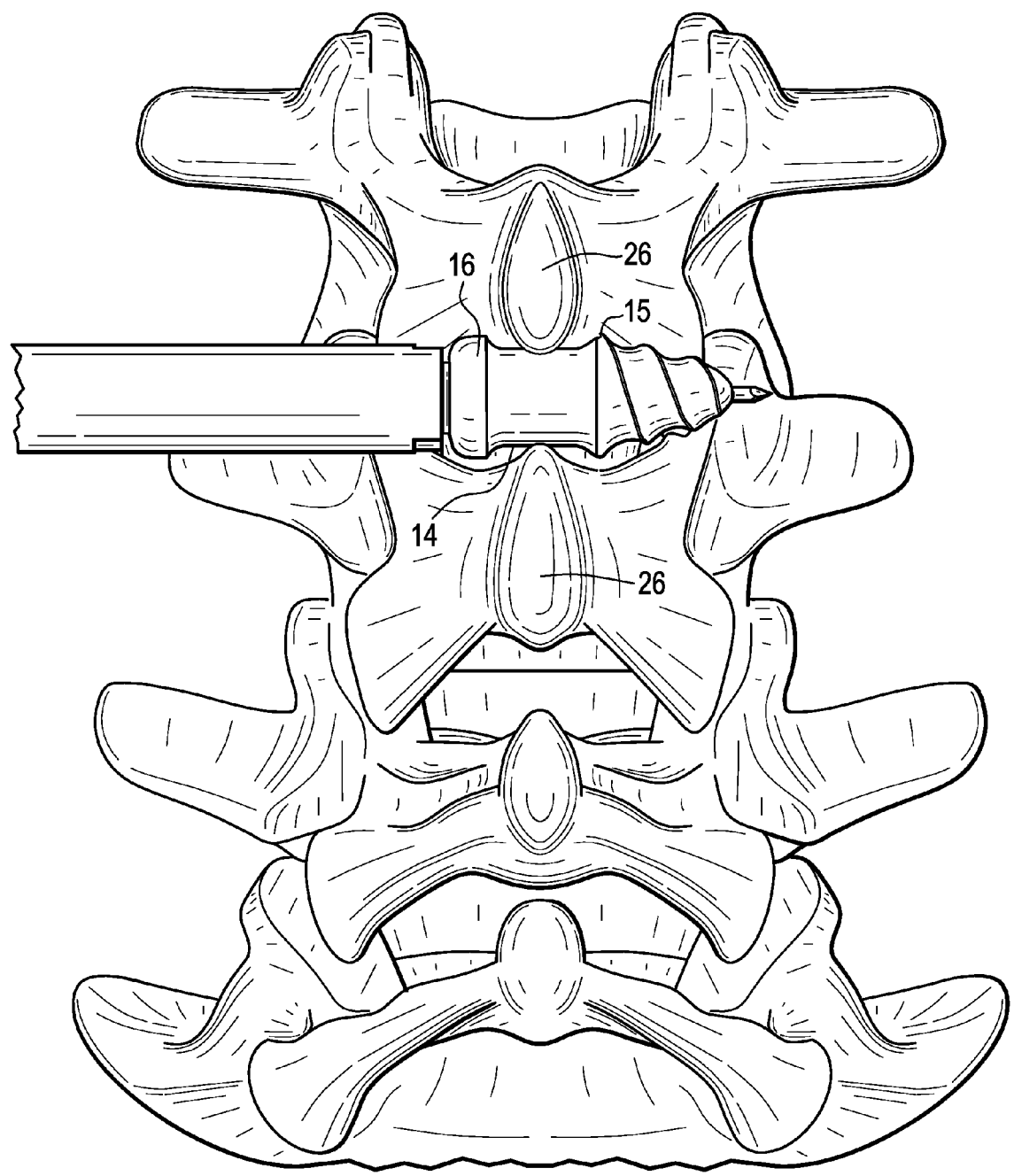

The method further includes implanting the distractor 12 between the two spinous processes 26 such that the two spinous processes 26 rest in the central engagement groove 14 between a proximal end 15 and a distal end 16 of the central engagement groove 14 (FIG. 13E).

Figure 13F:
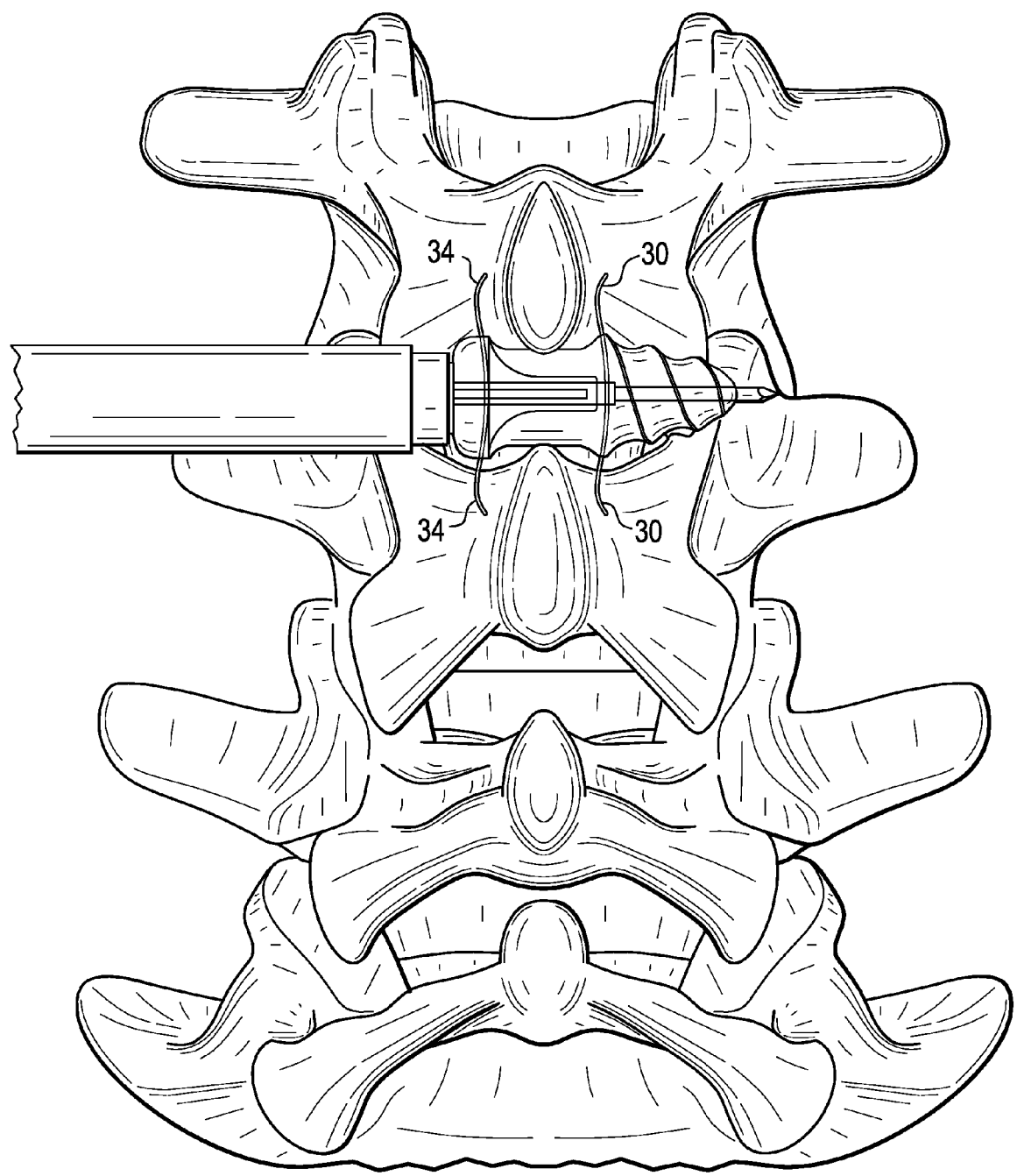
Figure 13G:
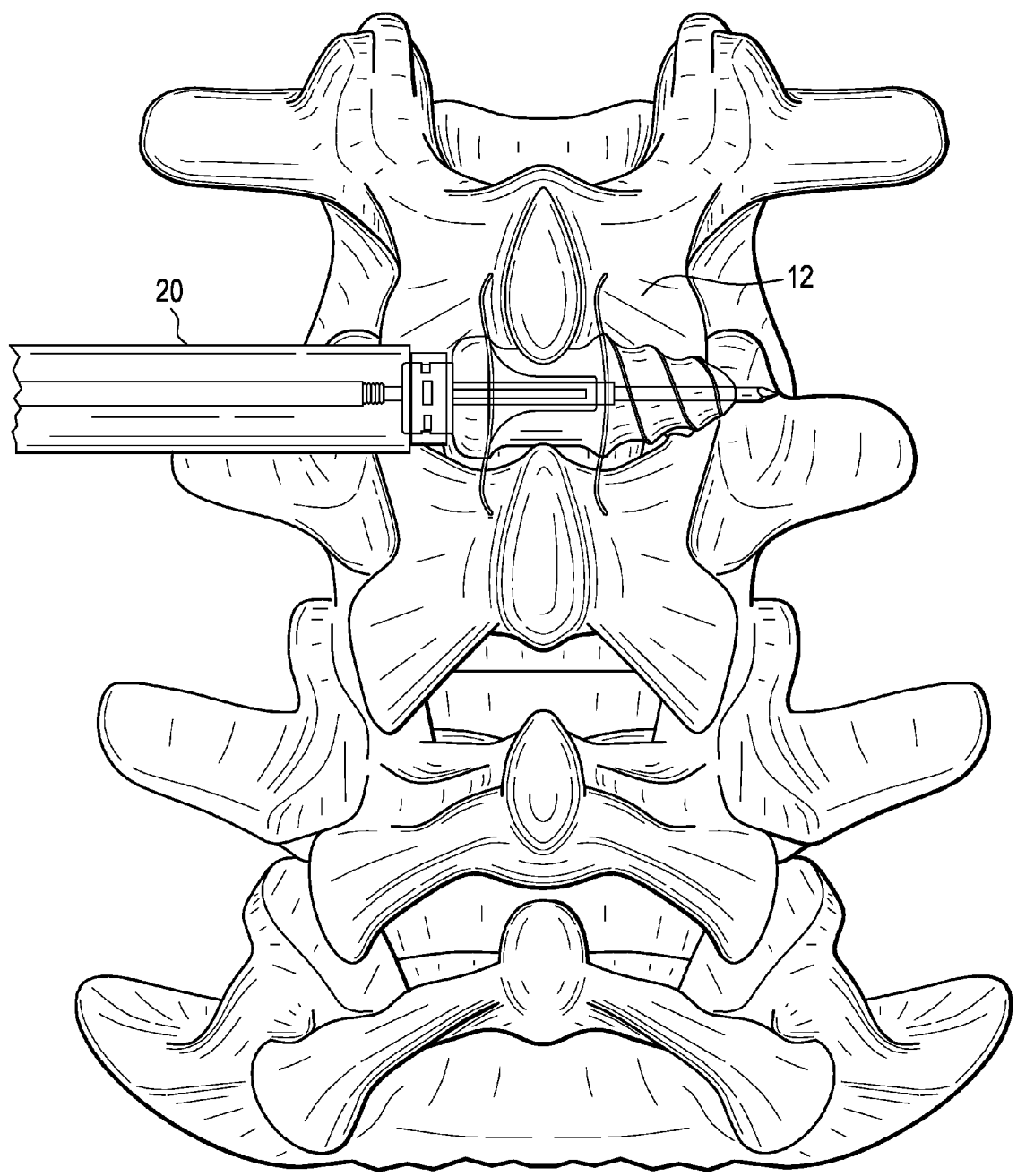
Figure 13H:
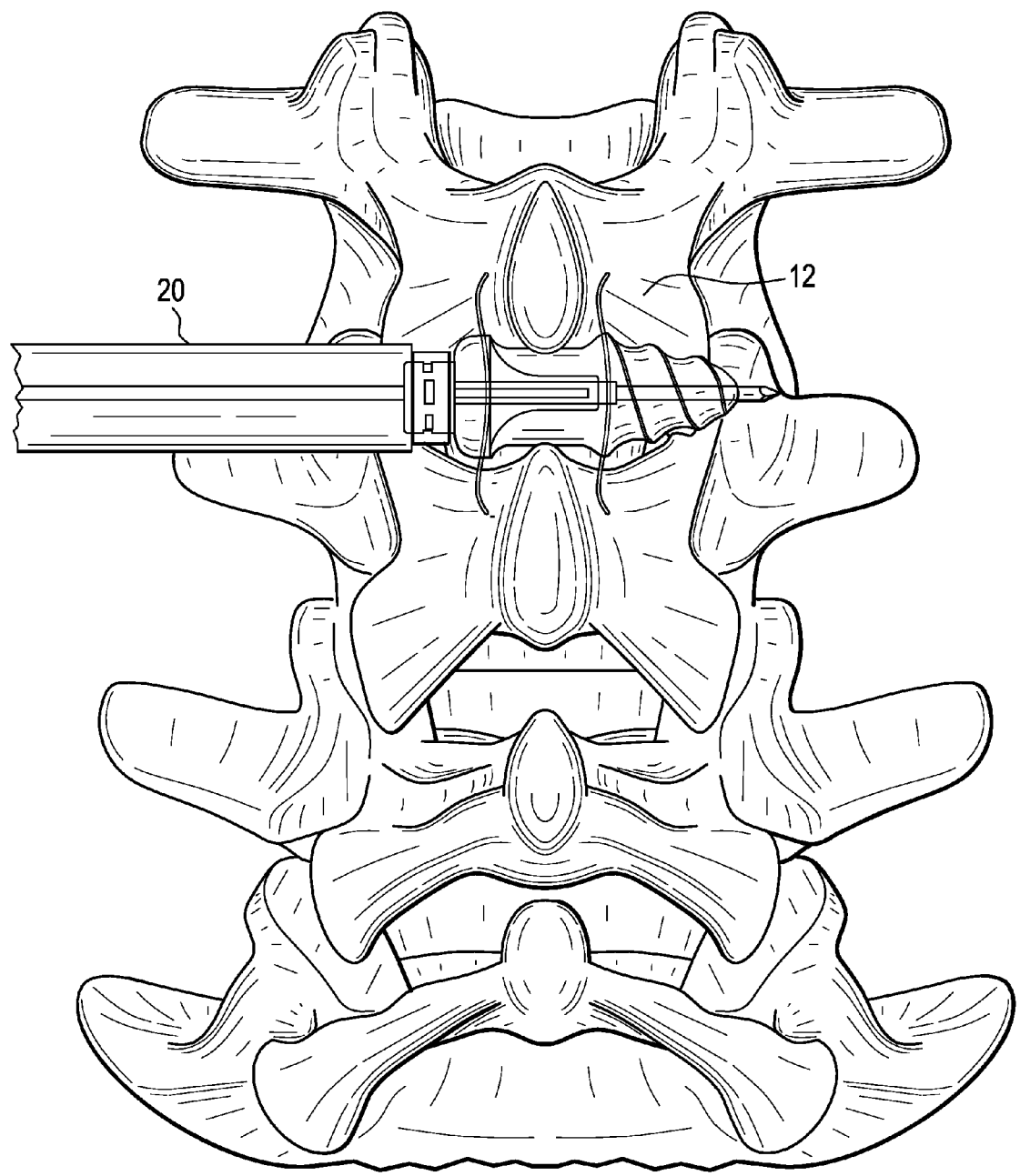

The method further includes deploying a stabilizer (e.g., stabilization wings 30 and 34) which is adapted to be deployed from within the distractor 12 to secure the two spinous processes 26 within the central engagement groove 14 (FIG. 13F). The stabilizer may also be locked into the deployed state (FIG. 13F).

Figure 13I:
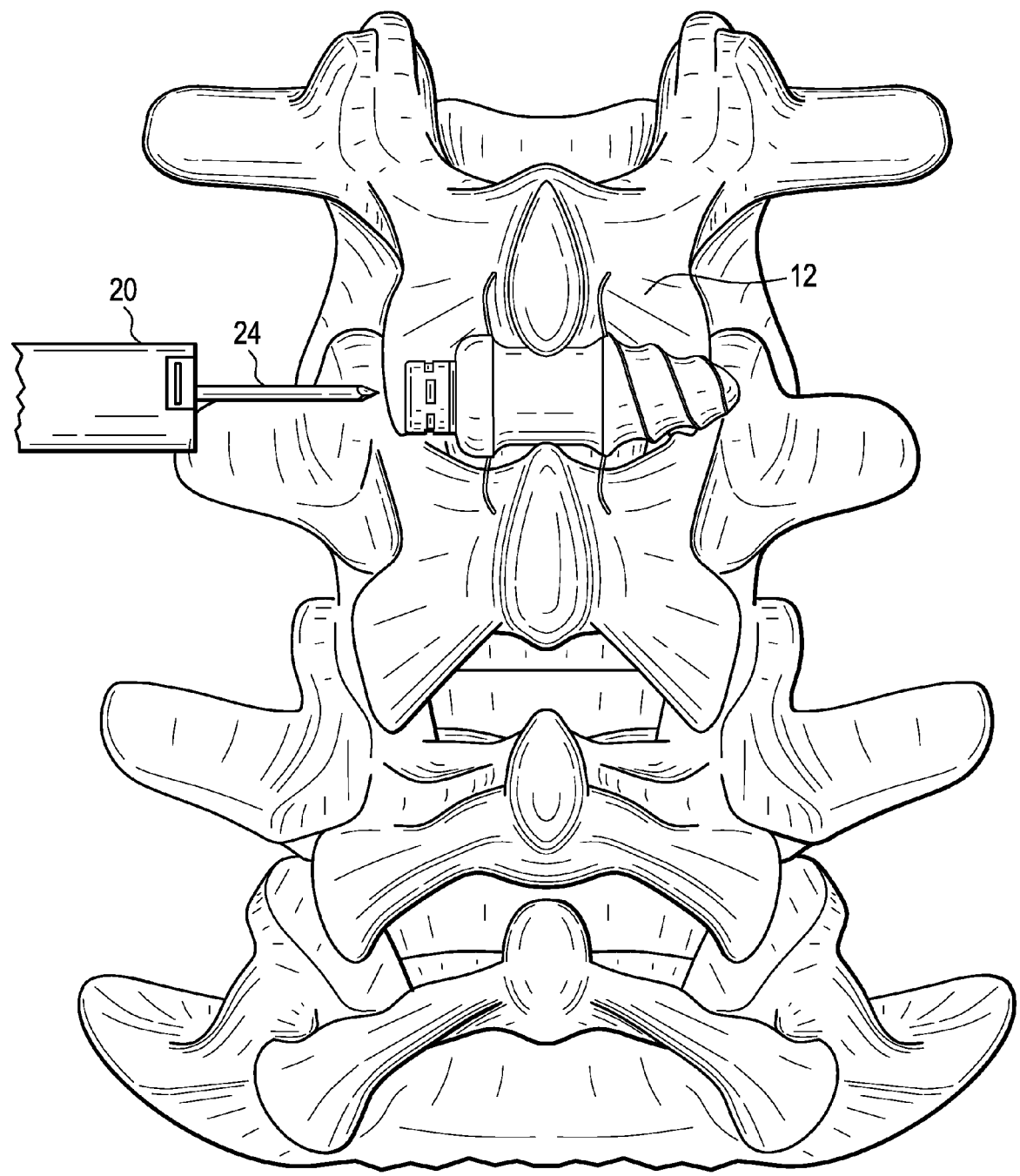

The method further includes decoupling the insertion driver 20 from the distractor 12 (FIG. 13G and 13H) and removing the insertion driver 20 and the guide wire 24 (FIG. 13I).

What is claimed is:
1. A conical interspinous apparatus comprising:
 a distractor comprising an insertion portion and a central engagement groove having a proximal end and a distal end, the insertion portion having a conical shape which tapers from the proximal end of the central engagement groove to a tip and is adapted to enable passage of the distractor between two spinous processes of vertebrae such that a gradual distraction between the two spinous processes occurs, and the central engagement groove is adapted to secure the distractor between the two spinous processes such that the two spinous processes rest in the central engagement groove between the proximal end and the distal end; and an insertion driver detachably coupled to a rear portion of the distractor; and wherein the distractor and the insertion driver each have a guide channel extending through an entire central portion therein, each guide channel being in alignment with each other;

a stabilizer which is adapted to be deployed from the distractor to secure the two spinous processes within the central engagement groove, wherein the stabilizer comprises:

a wire fed through the guide channel and connected to the tip of the insertion portion; and the insertion portion, made of flexible material and having a first diameter at the proximal end of the central engagement groove, is configured to collapse towards the proximal end of the central engagement groove such that the insertion portion is compressed into a shape having a second diameter at the proximal end of the central engagement groove larger than the first diameter to inhibit the distractor from reversing out from between the two spinous processes, the tip of the insertion portion is adapted to be pulled towards the central engagement groove upon pulling of the wire to collapse the insertion portion.

2. The conical interspinous apparatus of claim 1, the stabilizer further comprising a stabilization base coupled to the distal end of the central engagement groove and which extends outward from the distractor and is adapted to inhibit the distractor from being inserted further between the two spinous processes.

3. A conical interspinous apparatus comprising:

a distractor comprising an insertion portion and a central engagement groove having a proximal end and a distal end, the insertion portion having a conical shape which tapers from the proximal end of the central engagement groove to a tip and is adapted to enable passage of the distractor between two spinous processes of vertebrae such that a gradual distraction between the two spinous processes occurs, and the central engagement groove is adapted to secure the distractor between the two spinous processes such that the two spinous processes rest in the central engagement groove between the proximal end and the distal end; and an insertion driver detachably coupled to a rear portion of the distractor; and wherein the distractor and the insertion driver each have a guide channel extending through an entire central portion therein, each guide channel being in alignment with each other;

a stabilizer which is adapted to be deployed from the distractor to secure the two spinous processes within the central engagement groove, wherein the stabilizer comprises:

a pair of proximal stabilization wings retracted within a first cavity of the distractor and configured to be deployed through a pair of proximal slots disposed on opposite sides of the proximal end of the central engagement groove; and an insertion screw driver inserted within the guide channel of the distractor, coupled to the insertion driver and configured to engage a first pair of gears, each gear of the first pair of gears mechanically coupled to one of the pair of proximal stabilization wings, wherein when the insertion driver is turned, the insertion screw driver is turned within the distractor and engages with the first pair of gears to deploy the pair of proximal stabilization wings from the proximal slots.

4. The conical interspinous apparatus of claim 3, wherein the stabilizer further comprises:

a pair of distal stabilization wings retracted within a second cavity of the distractor and configured to be deployed through a pair of distal slots disposed on opposite sides of the distal end of the central engagement groove; and the insertion screw driver is configured to engage a second pair of gears, each gear of the second pair of gears mechanically coupled to one of the pair of distal stabilization wings, wherein when the insertion driver is turned, the insertion screw driver is turned within the distractor and engages with the second pair of gears to deploy the pair of distal stabilization wings from the distal slots.

5. The conical interspinous apparatus of claim 3, the stabilizer further comprising a stabilization base coupled to the distal end of the central engagement groove and which extends outward from the distractor and is adapted to inhibit the distractor from being inserted further between the two spinous processes.

6. The conical interspinous apparatus of claim 3, further comprising:

a guide wire having a pointed tip, the guide wire being adapted for insertion between the two spinous processes and configured to guide the insertion of the distractor, coupled to the insertion driver, between the two spinous processes, wherein the guide channel of each of the distractor and the insertion driver is configured to accept the guide wire therein.

7. The conical interspinous apparatus of claim 3, wherein the distractor is composed of at least one of poly-ether-etherketone (PEEK), titanium, stainless steel, bone, hydroxyapatite, bone substitutes, a combination of hydroxyapatite and bone cement, and CORTOSS.

8. A conical interspinous apparatus comprising:

a distractor comprising an insertion portion and a central engagement groove having a proximal end and a distal end, the insertion portion having a conical shape which tapers from the proximal end of the central engagement groove to a tip and is adapted to enable passage of the distractor between two spinous processes of vertebrae such that a gradual distraction between the two spinous processes occurs, and the central engagement groove is adapted to secure the distractor between the two spinous processes such that the two spinous processes rest in the central engagement groove between the proximal end and the distal end; and an insertion driver detachably coupled to a rear portion of the distractor; and wherein the distractor and the insertion driver each have a guide channel extending through an entire central portion therein, each guide channel being in alignment with each other;

a stabilizer which is adapted to be deployed from the distractor to secure the two spinous processes within the central engagement groove, wherein the stabilizer comprises:

a pair of proximal stabilization wings retracted within a first cavity of the distractor and configured to be deployed through a pair of proximal slots disposed on opposite sides of the proximal end of the central engagement groove;

a pair of distal stabilization wings retracted within a second cavity of the distractor and configured to be deployed through a pair of distal slots disposed on opposite sides of the distal end of the central engagement groove; and a deployment bar coupled to the insertion driver and to each stabilization wing of the proximal stabilization wings and the distal stabilization wings, the deployment bar being inserted within the guide channel of the distractor, and configured to be slidably switched between an extended position and a retracted position, wherein, when in the extended position, the deployment bar maintains the proximal stabilization wings and the distal stabilization wings in a retracted state, and, when in the retracted position, the deployment bar releases the proximal stabilization wings and the distal stabilization wings to a deployed state.

9. The conical interspinous apparatus of claim 8, wherein the stabilizer further comprises:

a lock configured to engage with the deployment bar while in the retracted position and configured to turn the deployment bar to lock each of the stabilization wings of the proximal stabilization wings and the distal stabilization wings into the deployed state.

10. The conical interspinous apparatus of claim 8, further comprising:

a guide wire having a pointed tip, the guide wire being adapted for insertion between the two spinous processes and configured to guide the insertion of the distractor, coupled to the insertion driver, between the two spinous processes, wherein the guide channel of each of the distractor and the insertion driver is configured to accept the guide wire therein.

11. The conical interspinous apparatus of claim 8, wherein the distractor is composed of at least one of poly-ether-ether-ketone (PEEK), titanium, stainless steel, bone, hydroxyapatite, bone substitutes, a combination of hydroxyapatite and bone cement, and CORTOSS.

12. A conical interspinous apparatus comprising:

a distractor comprising an insertion portion and a central engagement groove having a proximal end and a distal end, the insertion portion having a conical shape which tapers from the proximal end of the central engagement groove to a tip and is adapted to enable passage of the distractor between two spinous processes of vertebrae such that a gradual distraction between the two spinous processes occurs, and the central engagement groove is adapted to secure the distractor between the two spinous processes such that the two spinous processes rest in the central engagement groove between the proximal end and the distal end; and a stabilizer which is adapted to be deployed from the distractor to secure the two spinous processes within the central engagement groove, wherein the stabilizer comprises:

a pair of proximal stabilization wings retracted within a first cavity of the distractor and configured to be deployed through a pair of proximal slots disposed on opposite sides of the proximal end of the central engagement groove; and a pair of distal stabilization wings retracted within a second cavity of the distractor and configured to be deployed through a pair of distal slots disposed on opposite sides of the distal end of the central engagement groove, wherein the pair of proximal stabilization wings and the pair of distal stabilization wings are coupled to the central engagement groove by a pressure mechanism such that the stabilization wings are deployed when the central engagement groove is pressurized by compression from the two spinous processes upon insertion therebetween.

13. The conical interspinous apparatus of claim 12, further comprising:

a guide wire having a pointed tip, the guide wire being adapted for insertion between the two spinous processes and configured to guide the insertion of the distractor, coupled to the insertion driver, between the two spinous processes, wherein a guide channel of each of the distractor and the insertion driver is configured to accept the guide wire therein.

14. A conical interspinous apparatus comprising:

a distractor comprising an insertion portion and a central engagement groove having a proximal end and a distal end, the insertion portion having a conical shape which tapers from the proximal end of the central engagement groove to a tip and is adapted to enable passage of the distractor between two spinous processes of vertebrae such that a gradual distraction between the two spinous processes occurs, and the central engagement groove is adapted to secure the distractor between the two spinous processes such that the two spinous processes rest in the central engagement groove between the proximal end and the distal end; and a stabilizer which is adapted to be deployed from the distractor to secure the two spinous processes within the central engagement groove, wherein the stabilizer comprises:

a pair of proximal stabilization wings retracted within a first cavity of the distractor and configured to be deployed through a pair of proximal slots disposed on opposite sides of the proximal end of the central engagement groove, the proximal stabilization wings are balloon O-rings such that the proximal stabilization wings are deflated in a retracted state and inflated in a deployed state;

a pair of distal stabilization wings retracted within a second cavity of the distractor and configured to be deployed through a pair of distal slots disposed on opposite sides of the distal end of the central engagement groove, the distal stabilization wings are balloon O-rings such that the distal stabilization wings are deflated in a retracted state and inflated in a deployed state; and a pump coupled to each of the proximal stabilization wings and distal stabilization wings to inflate the proximal stabilization wings and the distal stabilization wings to a deployed state.

15. The conical interspinous apparatus of claim 14, further comprising:

a guide wire having a pointed tip, the guide wire being adapted for insertion between the two spinous processes and configured to guide the insertion of the distractor, coupled to the insertion driver, between the two spinous processes, wherein a guide channel of each of the distractor and the insertion driver is configured to accept the guide wire therein.

16. A conical interspinous apparatus comprising:

a distractor comprising an insertion portion and a central engagement groove having a proximal end and a distal end, the insertion portion having a conical shape which tapers from the proximal end of the central engagement groove to a tip and is adapted to enable passage of the distractor between two spinous processes of vertebrae such that a gradual distraction between the two spinous processes occurs, and the central engagement groove is adapted to secure the distractor between the two spinous processes such that the two spinous processes rest in the central engagement groove between the proximal end and the distal end, wherein the insertion portion includes a pair of axial rectangular grooves, each disposed oppositely from each other, and a stabilizer which is adapted to be deployed from the distractor to secure the two spinous processes within the central engagement groove, the stabilizer comprises:

a pair of side wings, each disposed within one of the pair of axial rectangular grooves and are configured to be congruent with a shape of the axial rectangular grooves and with a surface of the insertion portion in an undeployed state, the pair of side wings configured to be deployed outward from the axial rectangular grooves;

a deployment means which deploys the pair of side wings from the axial rectangular grooves by pulling the side wings towards the proximal end of the central engagement groove such that such that the side wings open up from the axial rectangular grooves to a vertical position adjacent to the proximal end of the central engagement groove; and a pair of hinges, each hinge coupling the deployment means to a distal end of each of the side wings, enabling the side wings to open to a deployed state.

17. The conical interspinous apparatus of claim 16, wherein the insertion portion has a conical screw shape such that the surface of the insertion portion has screw-shaped grooves adapted to enable the distractor to be screwed into place between the two spinous processes.

18. The conical interspinous apparatus of claim 16, the stabilizer further comprising a stabilization base coupled to the distal end of the central engagement groove and which extends outward from the distractor and is adapted to inhibit the distractor from being inserted further between the two spinous processes.

19. The conical interspinous apparatus of claim 16, further comprising:

a guide wire having a pointed tip, the guide wire being adapted for insertion between the two spinous processes and configured to guide the insertion of the distractor, coupled to the insertion driver, between the two spinous processes, wherein a guide channel of each of the distractor and the insertion driver is configured to accept the guide wire therein.

20. The conical interspinous apparatus of claim 16, wherein the distractor is composed of at least one of polyether-ether-ketone (PEEK), titanium, stainless steel, bone, hydroxyapatite, bone substitutes, a combination of hydroxyapatite and bone cement, and CORTOSS.

21. A conical interspinous apparatus comprising:

a distractor comprising an insertion portion and a central engagement groove having a proximal end and a distal end, the insertion portion having a conical shape which tapers from the proximal end of the central engagement groove to a tip and is adapted to enable passage of the distractor between two spinous processes of vertebrae such that a gradual distraction between the two spinous processes occurs, and the central engagement groove is adapted to secure the distractor between the two spinous processes such that the two spinous processes rest in the central engagement groove between the proximal end and the distal end;

an insertion driver detachably coupled to a rear portion of the distractor;

a pair of proximal stabilization wings retracted within a first cavity of the distractor and configured to be deployed through a pair of proximal slots disposed on opposite sides of the proximal end of the central engagement groove;

a pair of distal stabilization wings retracted within a second cavity of the distractor and configured to be deployed through a pair of distal slots disposed on opposite sides of the distal end of the central engagement groove;

a deployment mechanism coupled to the insertion driver and to the proximal and distal stabilization wings, the deployment mechanism configured to move the proximal stabilization wings and the distal stabilization wings from a retracted state to a deployed state to secure the two spinous processes within the central engagement groove.

22. The conical interspinous apparatus of claim 21, wherein the distractor and the insertion driver each have a guide channel extending through an entire central portion therein, each guide channel being in alignment with each other.

23. The conical interspinous apparatus of claim 22, further comprising:

a guide wire having a pointed tip, the guide wire being adapted for insertion between the two spinous processes and configured to guide the insertion of the distractor, coupled to the insertion driver, between the two spinous processes, wherein the guide channel of each of the distractor and the insertion driver is configured to accept the guide wire therein.

24. The conical interspinous apparatus of claim 22, wherein the deployment mechanism comprises:

an insertion screw driver inserted within the guide channel of the distractor, coupled to the insertion driver and configured to engage a first pair of gears and a second pair of gears, the first pair of gears mechanically coupled the pair of proximal stabilization wings and the second pair of gears mechanically coupled to the pair of distal stabilization wings, wherein, when the insertion driver is turned, the insertion screw driver is turned within the distractor and engages with the first and second pair of gears to deploy the pair of proximal stabilization wings from the proximal slots and the pair of distal stabilization wings from the distal slots.

25. The conical interspinous apparatus of claim 22, wherein the deployment mechanism comprises:

a deployment bar coupled to the insertion driver end to each stabilization wing of the proximal stabilization wings and the distal stabilization wings, the deployment bar being inserted within the guide channel of the distractor, and configured to be slidably switched between an extended position and retracted position, wherein, when in the extended position, the deployment bar maintains the proximal stabilization wings and the distal stabilization wings in a retracted state, and, when in the retracted position, the deployment bar releases the proximal stabilization wings and the distal stabilization wings to a deployed state.

26. The conical interspinous apparatus of claim 25, wherein the deployment mechanism further comprises:

a lock configured to engage with the deployment bar while in the retracted position and configured to turn the deployment bar to lock each of the stabilization wings of the proximal stabilization wings and the distal stabilization wings into the deployed state.

27. The conical interspinous apparatus of claim 21, wherein the insertion portion has a conical screw shape such that a surface of the insertion portion has screw-shaped grooves adapted to enable the distractor to be screwed into place between the two spinous processes.

28. The conical interspinous apparatus of claim 27, wherein the tip of the insertion portion is ungrooved.

29. The conical interspinous apparatus of claim 21, wherein the distractor is composed of at least one of poly-ether-ether-ketone (PEEK), titanium, stainless steel, bone, hydroxyapatite, bone substitutes, a combination of hydroxyapatite and bone cement, and CORTOSS.

* * * * *